US008557560B2

(12) United States Patent
Martín Jiménez et al.

(10) Patent No.: US 8,557,560 B2
(45) Date of Patent: Oct. 15, 2013

(54) MAMMALIAN MILK MICROORGANISMS, COMPOSITIONS CONTAINING THEM AND THEIR USE FOR THE TREATMENT OF MASTITIS

(75) Inventors: Rocio Martín Jiménez, Algeciras-Cádiz (ES); Mónica Olivares Martín, Huetor Vega-Granada (ES); Esther Antonia Jiménez Quintana, Los Molinos-Madrid (ES); Maria Luisa Marín Martínez, Madrid (ES); Saleta Sierra Ávila, Granada (ES); Antonio Maldonado Barragán, Corla del Rio-Sevilla (ES); Virginia Martín Merino, Madrid (ES); Francesc Blanch Martell, Barcelona (ES); Celina Torre Lloveras, Sant Cugat del Vallés-Barcelona (ES); Federico Lara Villoslada, Albolote-Granada (ES); Rebeca Arroyo Rodríguez, Torrejón de Ardoz-Madrid (ES); Julio Boza Puerta, Granada (ES); Jesús Jiménez López, Granada (ES); Leónides Fernández Álvarez, Madrid (ES); Odón Julían Sobrino Abuja, Pozuelo de Alarcón-Madrid (ES); Jordi Xaus Pei, Granada (ES); Juan Miguel Rodríguez Gómez, Colmenar Viejo-Madrid (ES); Susana Delgado Palacio, Oviedo-Asturias (ES)

(73) Assignee: Puleva Biotech, S.A., Granada (ES)

( * ) Notice: Subject to any disclaimer, the term of this patent is extended or adjusted under 35 U.S.C. 154(b) by 0 days.

(21) Appl. No.: 12/602,182

(22) PCT Filed: Jun. 2, 2008

(86) PCT No.: PCT/EP2008/056768
§ 371 (c)(1),
(2), (4) Date: Jun. 25, 2010

(87) PCT Pub. No.: WO2008/145756
PCT Pub. Date: Dec. 4, 2008

(65) Prior Publication Data
US 2010/0266550 A1 Oct. 21, 2010

(30) Foreign Application Priority Data
May 31, 2007 (EP) .................................. 07380158

(51) Int. Cl.
C12N 1/20 (2006.01)
C12N 1/12 (2006.01)
A01N 63/00 (2006.01)

(52) U.S. Cl.
USPC ................. 435/252.9; 435/252.1; 424/93.4; 424/93.45

(58) Field of Classification Search
USPC ............ 424/93.3, 93.4, 93.45; 435/34, 252.1, 435/252.9
See application file for complete search history.

(56) References Cited

U.S. PATENT DOCUMENTS

| 4,591,499 A | 5/1986 | Linn et al. | |
|---|---|---|---|
| 7,468,270 B2 * | 12/2008 | Xaus Pei et al. | ............ 435/252.9 |
| 2006/0093594 A1 * | 5/2006 | Naidu | ........................ 424/93.45 |

FOREIGN PATENT DOCUMENTS

| EP | 0577904 A1 | 7/1992 |
|---|---|---|
| WO | 9746104 A1 | 12/1997 |
| WO | 2004003235 A2 | 1/2004 |
| WO | 2005034970 A1 | 4/2005 |
| WO | 2005117532 A2 | 12/2005 |

OTHER PUBLICATIONS

S. P. Oliver et al., "Prevention of bovine mastitis by a *Lactobacillus acidophilus* preparation." J. Dairy Science (1985) vol. 68, No. Suppl. 1 pp. 271, 62nd Annual Meeting of the American Dairy Science Association, Feb. 3-6, 1985.*
M. Al-Qumber et al., "Commensal bacilli inhibitory to mastitis pathogens isolated from the udder microbiota of healthy cows." J. Appl. Microbiology vol. 101, (2006) 1152-1160.*
Olivares, M., et al., Antimicrobial potential of four *Lactobacillus* strains isolated from breast milk, Journal of Applied Microbiology, 2006, pp. 72-79, vol. 101.
Kaur, Indu Pal, et al, Probiotics: potential pharmaceutical applications, European Journal of Pharmaceutical Sciences, 2002, pp. 1-9, vol. 15.
Heikkila, M.P., et al., Inhibition of *Staphylococcus aureus* by teh commensal bacteria of human milk, Journal of Applied Microbiology, 2003, pp. 471-478, vol. 95.
Gill, J.J., et al., Efficacy and Pharmacokinetics of Bacteriophage Therapy in Treatment of Subclinical *Staphylococcus aureus* Mastitis in Lactating Dairy Cattle, Antimocrobial Agents and Chemotherapy, Sep. 2006, pp. 2912-2918, vol. 50, No. 9.

(Continued)

Primary Examiner — Blaine Lankford, Jr.
Assistant Examiner — Charles Z Constantine
(74) Attorney, Agent, or Firm — Tristan A. Fuierer; Moore & Van Allen, PLLC

(57) ABSTRACT

The present invention relates to a novel approach to prevent or treat mastitis both in humans and animals through the use of mammal milk-derived microorganisms obtained from healthy hosts of the homologous species; to those new probiotic microorganisms obtained from milk able to reduce infectious mastitis and the method of screening used for their obtaining; to the use of these probiotic bacteria for the prophylaxis or treatment against mastitis and other diseases; and finally, to compositions comprising these compounds.

10 Claims, 12 Drawing Sheets

(56) References Cited

OTHER PUBLICATIONS

Greene, W.A., et al., Comparison of Probiotic and Antibiotic Intramammary Therapy of Cattle with Elevated Somatic Cell Counts, Journal of Dairy Science, 1991, pp. 2976-2981, vol. 74.

Jacobsen, C.N., et al., Screening of Probiotic Activities of Forty-Seven Strains of *Lactobacillus* spp. by in Vitro Techniques and Evaluation of the Colonization Ability of Five Selected Strains in Humans, Applied and Environmental Microbiology, Nov. 1999, pp. 4949-4956, vol. 65, No. 11.

Lowy, M.D., Franklin D., *Staphylococcus aureus* Infections, The New England Journal of Medicine, Aug. 20, 1998, pp. 520-532, vol. 339.

Takahashi, Hideyuki, et al., Effect of intramammary injection of rboGM-CSF on milk levels of chemiluminescenece activity, somatic cell count, and *Staphylococcus aureus* count in Holstein cows with S. aureus subclinical mastitis, The Canadian Journal of Veterinary Research, 2004, pp. 182-187, vol. 68.

* cited by examiner

*Bifidobacterium breve* (CECT under Accession N° 7263)

TCGNGTNNGAAGNACAATAAACACNTAAGTGCCTTGCTCCCTAACAAAAGA
GGTTTACAACCCGCAAGGCCTCCATCCCTCACGCGGCGTCGCTGCATCAG
GCTTGCGCCCATTGATGCAATATTCCCCANTGCTGCCTCCCGATANGAGT
CTGGGCCGTATCTCAGTCCCAATGTGGCCGGTCGCCCTCTCAGGCCGGC
TACCCGTCGAAGCCATGGTGGGCCGTTACCCCGCCATCAAGCTGATAGGA
CGCGACCCCATCCCATGCCGCAAAGGCTTTCCCAACACACCATGCGGTGT
GATGGAGCATCCGGCATTACCACCCGTTTCCAGGAGCTATTCCGGTGCAT
GGGGCAGGTCGGTCACGCATTACTCACCCGTTCGCCACTCTCACCACCAG
GCAAAGCCCGATGGATCCCGTTCGACTTGCATGTGTTAAGCACGCCGCCA
GCGTTCATCCTGAGCCAGGATCAAACTCTAA

*Bifidobacterium breve* (CECT under Accession N° 7264)

TNCGCGANGAAGAAATAAAACAAAGTGCCTTGCTCCTAACAAAAGAGGTT
TACAACCCGAANGCCTCCATNCCTCACGNGGNGTCNCATGCATCAGGCTT
GCGCCCATTGTGNAATATTCCCCACTGCTGCCTCCCGTANGAGTCTGGGC
CGTATCTNANTCCCAATGTGGCCGGTCGCCCTCTCAGGCCGGCTACCCGT
CGAAGCCATGGTGGGCCGTTACCCCGCCATCAAGCTGATAGGACGCGAC
CCCATCCCATGCCGCAAAGGCTTTCCCAACACACCATGCGGTGTGATGGA
GCATCCGGCATTACCACCCGTTTGCAGGAGCTATTCCGGTGCATGGGGCA
GGTCNGTACGCATTACTNACCCGTTCGCCACTCTCACCACCAGGCAAAG
CCCGATGGATCCCGTTCGACTTGCATGTGTTAAGCACGCCGCCNGCGTTC
ATCCNNAAACAGGATCAAACTCTAAA

*Lactobacillus reuteri* (CECT under Accession N° 7260)

GCNTGGGNGAACGGTCACTGCGGAACAGTTACTCTCACGCACGTTCTTCTCCAACAACA
GAGCTTTACGAGCCGAAACCCTTCTTCACTCACGCGGTGTTGCTCCATCAGGCTTGCGC
CCATTGTGGAAGATTCCCTACTGCTGCCTCCCGTAGGAGTATGGACCGTGTCTCAGTTC
CATTGTGGCCGATCAGTCTCTCAACTCGGCTATGCATCATCGCCTTGGTAAGCCGTTAC
CTTACCAACTAGCTAATGCACCGCAGGTCCATCCCAGAGTGATAGCCAAAGCCATCTTT
CAAACAAAAGCCATGTGGCTTTTGTTGTTATGCGGTATTAGCATCTGTTTCCAAATGTT
ATCCCCCGCTCCGGGGCAGGTTACCTACGTGTTACTCACCCGTCCGCCACTCACTGGTG
ATCCATCGTCAATCAGGTGCAAGCACCATCAATCAGTTGGGCCAGTGCGTACGACTTGC
ATGTATTAGGCACACCGCCGGCGTTCATCCTGAGNCAGGATCNAAACTCTAA

*Lactobacillus plantarum* (CECT under Accession N° 7262)

GGCCTGGGAANCCGGTCATACCTGGAACAGGTTACCTCTCAGATATGGTTCTTCTTTAA
CAACAGAGTTTTACGAGCCGAAACCCTTCTTCACTCACGCGGCGTTGCTCCATCAGACT
TTCGTCCATTGTGGAAGATTCCCTACTGCTGCCTCCCGTAGGAGTTTGGGCCGTGTCTC
AGTCCCAATGTGGCCGATTACCCTCTCAGGTCGGCTACGTATCATTGCCATGGTGAGCC
GTTACCTCACCATCTAGCTAATACGCCGCGGGACCATCCAAAAGTGATAGCCGAAGCCA
TCTTTCAAACTCGGACCATGCGGTCCAAGTTGTTATGCGGTATTAGCATCTGTTTCCAG
GTGTTATCCCCGCTTCTGGGCAGGTTTCCACGTGTTACTCACCAGTTCGCCACTCAC
TCAAATGTAATTCATGATGCAAGCACCAATCATTACCAGAGTTCGTTCGACTTGCATGT
ATTAGGCACGCCGCCAGCGTTCGTCCTGAGACAGGATCAAAACTCTA

Figure 1A

*Lactobacillus fermentum* (CECT under Accession N° 7265)

TACACGATATGAACAGNTTACCTCTCATACGGTGNTTCTTCTTTAACAACAGAGCTTTA
CGAGCCGAAACCCTTCTTCACTCACGCGGTGTTGCTCCATCAGGCTTGCGCCCATTGTG
GAAGATTCCCTACTGCTGCCTCCCGTAGGAGTATGGGCCGTGTCTCAGTCCCATTGTGG
CCGATCAGTCTCTCAACTCGGCTATGCATCATCGCCTTGGTAGGCCGTTACCCCACCAA
CAAGCTAATGCACCGCAGGTCCATCCAGAAGTGATAGCGAGAAGCCATCTTTTAAGCGT
TGTTCATGCGAACAACGNTGTTATGCGGTATTAGCATCTGTTTCCAAATGTTGTCCCCC
GCTTCTGGGCAGGTTACCTACGTGTTACTCACCCGTCCGCCACTCGTTGGCGACCAAAA
TCAATCAGGTGCAAGCACCATCAATCAATTGGGCCAACGCGTTCGACTTGCATGTATTA
GGCACACCGCCGGCGTTCATCCTGAGCCAGGATCAAANTCTAA

*Lactobacillus reuteri* (CECT under Accession N° 7266)

ACCGNGGGNNAACGACACTGCGNGNACAGNTTACTCTCACGCACGNTTCTTCTCCAACA
ACAGAGCTTTACGAGCCGAAACCCTTCTTCACTCACGCGGTGTTGCTCCATCAGGCTTG
CGCCCATTGTGGAAGATTCCCTACTGCTGCCTCCCGTAGGAGTATGGACCGTGTCTCAG
TTCCATTGTGGCCGATCAGTCTCTCAACTCGGCTATGCATCATCGCCTTGGTAAGCCGT
TACCTTACCAACTAGCTAATGCACCGCAGGTCCATCCCAGAGTGATAGCCAAAGCCATC
TTTCAAACAAAAGCCATGTGGCTTTTGTTGTTATGCGGTATTAGCATCTGTTTCCAAAT
GTTATCCCCGCTCCGGGGCAGGTTACCTACGTGTTACTCACCCGTCCGCCACTCACTG
GTGATCCATCGTCAATCAGGTGCAAGCACCATCAATCAGTTGGGCCAGTGCGTACGACT
TGCATGTATTAGGCACACCGCCGGCGTTCATCCTGAGCCAGGATCAAANTCTAA

*Enterococcus hirae* (CECT under Accession N° 7410)

GACAGTTACTCTCATCCTTGTTCTTCTCTAACAACAGAGTTTTACGATCCGAAAACCTT
CTTCACTCACGCGGCGTTGCTCGGTCAGACTTTCGTCCATTGCCGAAGATTCCCTACTG
CTGCCTCCCGTAGGAGTTTGGGCCGTGTCTCAGTCCCAATGTGGCCGATCACCCTCTCA
GGTCGGCTATGCATCGTCGCCTTGGTGAGCCGTTACCTCACCAACTAGCTAATGCACCG
CGGGTCCATCCATCAGCGACACCCGAAAGCGCCTTTCAAATCAAAACCATGCGGTTTCG
ATTGTTATACGGTATTAGCACCTGTTTCCAAGTGTTATCCCCTTCTGATGGGCAGGTTA
CCCACGTGTTACTCACCCGTTCGCCACTCCTCTTTTTCCGGTGGAGCAAGCTCCGGTGG
AAAAAGAAGCGTTCGACTTGCATGTATTAGGCACGCCGCCAGCGTTCGTCCTGAGCCAG
GT

*Lactobacillus plantarum* (CECT under Accession N° 7412)

TTACTCTCAGATATGTTCTTCTTTAACAACAGAGTTTTACGAGCCGAAACCCTTCTTCA
CTCACGCGGCGTTGCTCCATCAGACTTTCGTCCATTGTGGAAGATTCCCTACTGCTGCC
TCCCGTAGGAGTTTGGGCCGTGTCTCAGTCCCAATGTGGCCGATTACCCTCTCAGGTCG
GCTACGTATCATTGCCATGGTGAGCCGTTACCYCACCATCTAGCTAATACGCCGCGGGA
CCATCCAAAAGTGATAGCCGAAGCCATCTTTCAAGCTCGGACCATGCGGTCCAAGTTGT
TATGCGGTATTAGCATCTGTTTCCAGGTGTTATCCCCGCTTCTGGGCAGGTTTCCCAC
GTGTTACTCACCAGTTCGCCACTCACTCAAATGTAAATCATGATGCAAGCACCAATCAA
TACCAGAGTTCGTTCGACTTGCATGTATTAGGCACGCCGCCAGCGTTCGTCCTGAG

Figure 1B

*Enterococcus faecalis* (CECT under Accession Nº 7411)
CTATCATGCAAGTCGAACGCTTCTTTCCTCCCGAGTGCTTGCACTCAATTGGAAAGAGG
AGTGGCGGACGGGTGAGTAACACGTGGGTAACCTACCCATCAGAGGGGGATAACACTTG
GAAACAGGTGCTAATACCGCATAACAGTTTATGCCGCATGGCATAAGAGTGAAAGGCGC
TTTCGGGTGTCGCTGATGGATGGACCCGCGGTGCATTAGCTAGTTGGTGAGGTAACGGC
TCACCAAGGCCACGATGCATAGCCGACCTGAGAGGGTGATCGGCCACACTGGGACTGAG
ACACGGCCCAGACTCCTACGGGAGGCAGCAGTAGGGAATCTTCGGCAATGGACGAAAGT
CTGACCGAGCAACGCCGCGTGAGTGAAGAAGGTTTTCGGATCGTAAAACTCTGTTGTTA
GAGAAGAACAAGGACGTTAGTAACTGAACGTCCCCTGACGGTATCTAACCAGAAAGCCA
CGGCTAACTACGTGCCAGCA

*Lactobacillus salivarius* (CECT under Accession Nº 7409)
GGGTGGGGNGANCAGAACATGAAATGAACAGTTTACATCTCACCTCGCTGNTTCTTCCT
CTAACAACAGAGCTTTTACGACTCCGAAGGACCTTCTTCACATCACGCGGCGTNTGCTC
CATCAGACTTGCGTCCATTGTGGAAGATTCCCTACTGCTGCCTCCCGTAGGAGTTTGGG
CCGTGTCTCAGTCCCAATGTGGCCGATCAACCTCTCAGATTCGGCTACGTATCATCACC
TTGGTAGGCCGTTACCCCACCAACTAGTTAATACGCCGCGGGTCCATCTAAAAGCGATA
GNAGAACCATCTTTCATCTAAGGATCATGCGATCCTTAGAGATATACGGNATTAGCACC
TGTTTCCAAGTGTTATCCCCTTCTTTTAGGCAGGTTACCCACGTGTTACTCACCCGTCC
GCCACTCAACTTCTTACGGTGAATGCAAGCATTCGGTGTAAGAAAGTTTCGTTCGACTT
GCATGTATTAGGCACGCCGCCAGCGTTCGTNATGAGCCAGGATCAAACTCTA

*Lactobacillus reuteri* (CECT under Accession Nº 7413)
GCNTGGGNGAACGGTCACTGCGGAACAGTTACTCTCACGCACGTTCTTCTCCAACAACA
GAGCTTTACGAGCCGAAACCCTTCTTCACTCACGCGGTGTTGCTCCATCAGGCTTGCGC
CCATTGTGGAAGATTCCCTACTGCTGCCTCCCGTAGGAGTATGGACCGTGTCTCAGTTC
CATTGTGGCCGATCAGTCTCTCAACTCGGCTATGCATCATCGCCTTGGTAAGCCGTTAC
CTTACCAACTAGCTAATGCACCGCAGGTCCATCCCAGAGTGATAGCCAAAGCCATCTTT
CAAACAAAAGCCATGTGGCTTTTGTTGTTATGCGGTATTAGCATCTGTTTCCAAATGTT
ATCCCCCGCTCCGGGGCAGGTTACCTACGTGTTACTCACCCGTCCGCCACTCACTGGTG
ATCCATCGTCAATCAGGTGCAAGCACCATCAATCAGTTGGGCCAGTGCGTACGACTTGC
ATGTATTAGGCACACCGCCGGCGTTCATCCTGAGNCAGGATCNAAACTCTAA

Figure 1C

A
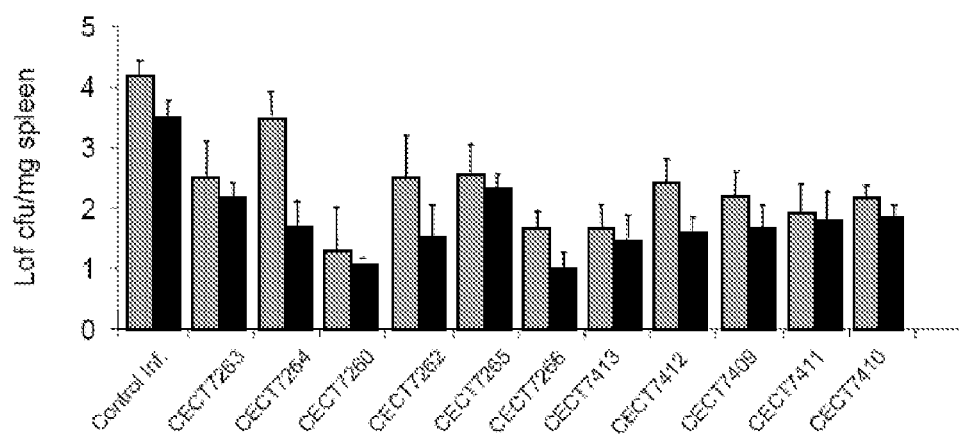
B
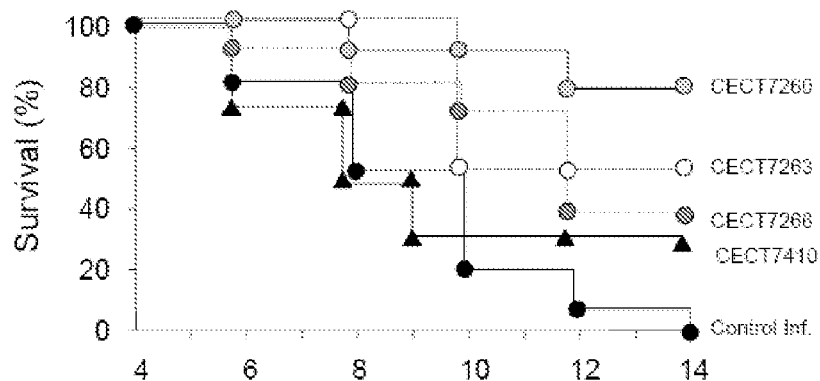
Figure 7

| TEST | 7263 | 7264 | 7260 | 7262 | 7265 | 7266 | PDA3 | LG14 | CELA203 | EFG1 | EHG11 |
|---|---|---|---|---|---|---|---|---|---|---|---|
| Glycerol | 0 | 0 | 0 | 0 | 0 | 0 | 0 | 0 | 0 | 0 | 0 |
| Erythritol | 0 | 0 | 0 | 0 | 0 | 0 | 0 | 0 | 0 | 0 | 0 |
| D-Arabinose | 0 | 0 | 0 | 5 | 0 | 5 | 5 | 0 | 0 | 5 | 5 |
| L-Arabinose | 0 | 0 | 0 | 5 | 0 | 5 | 5 | 5 | 0 | 1 | 0 |
| Ribose | 5 | 0 | 0 | 5 | 5 | 5 | 5 | 5 | 5 | 0 | 0 |
| D-Xylose | 0 | 0 | 0 | 0 | 0 | 0 | 0 | 0 | 0 | 5 | 5 |
| L-Xylose | 0 | 0 | 0 | 0 | 0 | 0 | 5 | 0 | 0 | 5 | 5 |
| Adonitol | 0 | 0 | 0 | 0 | 0 | 0 | 5 | 0 | 0 | 5 | 5 |
| β Methyl-xyloside | 0 | 0 | 0 | 0 | 0 | 5 | 0 | 0 | 0 | 0 | 0 |
| Galactose | 5 | 5 | 5 | 5 | 5 | 5 | 5 | 5 | 5 | 5 | 5 |
| D-Glucose | 5 | 5 | 5 | 5 | 5 | 0 | 0 | 5 | 5 | 0 | 0 |
| D-Fructose | 5 | 5 | 0 | 5 | 5 | 0 | 5 | 5 | 5 | 5 | 0 |
| D-Mannose | 1 | 0 | 0 | 0 | 0 | 5 | 0 | 0 | 0 | 0 | 0 |
| L-Sorbose | 0 | 0 | 0 | 0 | 0 | 0 | 0 | 0 | 0 | 5 | 0 |
| Rhamnose | 0 | 0 | 0 | 0 | 0 | 0 | 0 | 0 | 0 | 5 | 0 |
| Dulcitol | 0 | 0 | 0 | 0 | 0 | 0 | 0 | 0 | 0 | 0 | 0 |
| Inositol | 0 | 0 | 0 | 0 | 0 | 0 | 0 | 0 | 0 | 0 | 0 |
| Mannitol | 5 | 0 | 0 | 5 | 0 | 0 | 5 | 5 | 5 | 5 | 5 |
| Sorbitol | 0 | 0 | 0 | 5 | 5 | 0 | 5 | 0 | 0 | 5 | 5 |
| α Methyl-D-mannoside | 0 | 0 | 0 | 5 | 0 | 0 | 5 | 5 | 5 | 5 | 5 |
| α Methyl-D-glucoside | 0 | 1 | 0 | 5 | 5 | 0 | 5 | 5 | 0 | 5 | 5 |
| N Acetyl glucosamine | 2 | 1 | 0 | 5 | 0 | 0 | 5 | 5 | 0 | 5 | 5 |
| Amygdaline | 2 | 0 | 0 | 5 | 0 | 0 | 5 | 5 | 0 | 5 | 5 |
| Arbutine | 0 | 0 | 0 | 5 | 0 | 0 | 0 | 5 | 5 | 5 | 5 |
| Esculine | 5 | 5 | 0 | 5 | 5 | 0 | 5 | 5 | 5 | 5 | 5 |
| Salicine | 1 | 0 | 0 | 5 | 0 | 0 | 0 | 5 | 5 | 0 | 5 |
| Cellobiose | 5 | 0 | 0 | 5 | 0 | 0 | 5 | 5 | 5 | 0 | 5 |

FIGURE 9A

| TEST | 7263 | 7264 | 7260 | 7262 | 7265 | 7266 | PDA3 | LG14 | CELA200 | EFG1 | EHG11 |
|---|---|---|---|---|---|---|---|---|---|---|---|
| Maltose | 5 | 5 | 5 | 5 | 5 | 5 | 5 | 5 | 5 | 5 | 5 |
| Lactose | 5 | 0 | 5 | 5 | 5 | 5 | 5 | 5 | 5 | 0 | 0 |
| Melibiose | 5 | 5 | 5 | 5 | 5 | 5 | 5 | 5 | 5 | 5 | 0 |
| Saccharose | 5 | 0 | 5 | 0 | 5 | 0 | 0 | 0 | 5 | 0 | 0 |
| Trehalose | 0 | 0 | 0 | 5 | 5 | 0 | 0 | 5 | 5 | 1 | 5 |
| Inuline | 0 | 0 | 0 | 0 | 0 | 0 | 0 | 0 | 0 | 0 | 0 |
| Melezitose | 0 | 0 | 0 | 0 | 0 | 0 | 0 | 0 | 0 | 0 | 0 |
| D-Raffinose | 5 | 0 | 5 | 5 | 5 | 5 | 5 | 5 | 5 | 5 | 0 |
| Amidon | 5 | 5 | 0 | 0 | 0 | 0 | 0 | 0 | 0 | 5 | 0 |
| Glycogene | 0 | 0 | 0 | 0 | 0 | 0 | 5 | 0 | 0 | 0 | 0 |
| Xylitol | 0 | 0 | 0 | 0 | 0 | 0 | 0 | 0 | 0 | 0 | 0 |
| β-Gentiobiose | 0 | 2 | 0 | 5 | 0 | 0 | 0 | 5 | 0 | 5 | 0 |
| D-Turanose | 5 | 5 | 0 | 5 | 0 | 0 | 5 | 5 | 0 | 0 | 0 |
| D-Lyxose | 0 | 0 | 0 | 0 | 0 | 0 | 0 | 0 | 0 | 5 | 0 |
| D-Tagatose | 0 | 0 | 0 | 0 | 0 | 0 | 0 | 0 | 0 | 1 | 0 |
| D-Fucose | 0 | 0 | 0 | 0 | 0 | 0 | 0 | 0 | 0 | 0 | 0 |
| L-Fucose | 0 | 0 | 0 | 0 | 0 | 0 | 0 | 0 | 0 | 0 | 0 |
| D-Arabitol | 0 | 0 | 0 | 0 | 0 | 0 | 0 | 0 | 0 | 0 | 0 |
| L-Arabitol | 0 | 0 | 0 | 0 | 0 | 0 | 0 | 0 | 0 | 0 | 0 |
| Gluconate | 0 | 0 | 0 | 0 | 0 | 0 | 0 | 0 | 0 | 0 | 0 |
| 2 ceto-gluconate | 0 | 0 | 0 | 0 | 0 | 0 | 0 | 0 | 0 | 0 | 0 |
| 5 ceto-gluconate | 0 | 0 | 0 | 0 | 0 | 0 | 0 | 0 | 0 | 0 | 0 |

FIGURE 9B

SEQUENCE LISTING

```
<160> NUMBER OF SEQ ID NOS: 11

<210> SEQ ID NO 1
<211> LENGTH: 481
<212> TYPE: DNA
<213> ORGANISM: Bifidobacterium breve
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t

<400> SEQUENCE: 1
tcgngtnnga agnacaataa acacntaagt gccttgctcc ctaacaaaag aggtttacaa      60
cccgcaaggc ctccatccct cacgcggcgt cgctgcatca ggcttgcgcc cattgatgca     120
atattcccca ntgctgcctc ccgatangag tctgggccgt atctcagtcc caatgtggcc     180
ggtcgccctc tcaggccggc tacccgtcga agccatggtg ggccgttacc ccgccatcaa     240
gctgatagga cgcgacccca tcccatgccg caaaggcttt cccaacacac catgcggtgt     300
gatggagcat ccggcattac cacccgtttc caggagctat tccggtgcat ggggcaggtc     360
ggtcacgcat tactcacccg ttcgccactc tcaccaccag gcaaagcccg atggatcccg     420
ttcgacttgc atgtgttaag cacgccgcca gcgttcatcc tgagccagga tcaaactcta     480
a                                                                     481
```

```
<210> SEQ ID NO 2
<211> LENGTH: 476
<212> TYPE: DNA
<213> ORGANISM: Bifidobacterium breve
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (355)..(355)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t

<400> SEQUENCE: 2
tncgcganga agaaataaaa caaagtgcct tgctccctaa caaaagaggt ttacaacccg      60
aangcctcca tncctcacgn gggntcncat gcatcaggct tgcgcccatt gtgnaatatt     120
```

```
ccccactgct gcctcccgta ngagtctggg ccgtatctna ntcccaatgt ggccggtcgc    180
cctctcaggc cggctacccg tcgaagccat ggtgggccgt taccccgcca tcaagctgat    240
aggacgcgac cccatcccat gccgcaaagg cttccccaac acaccatgcg gtgtgatgga    300
gcatccggca ttaccacccg tttccaggag ctattccggt gcatggggca ggtcngtnac    360
gcattactna cccgttcgcc actctcacca ccaggcaaag cccgatggat cccgttcgac    420
ttgcatgtgt taagcacgcc gccngcgttc atccnnaaac aggatcaaac tctaaa        476
```

<210> SEQ ID NO 3
<211> LENGTH: 515
<212> TYPE: DNA
<213> ORGANISM: Lactobacillus fermentum
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (313)..(313)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t

<400> SEQUENCE: 3

```
tacacgatat gaacagntta cctctcatac ggtgnttctt ctttaacaac agagctttac     60
gagccgaaac ccttcttcac tcacgcggtg ttgctccatc aggcttgcgc ccattgtgga    120
agattcccta ctgctgcctc ccgtaggagt atgggccgtg tctcagtccc attgtggccg    180
atcagtctct caactcggct atgcatcatc gccttggtag gccgttaccc caccaacaag    240
ctaatgcacc gcaggtccat ccagaagtga tagcgagaag ccatctttta agcgttgttc    300
atgcgaacaa cgntgttatg cggtattagc atctgtttcc aaatgttgtc ccccgcttct    360
gggcaggtta cctacgtgtt actcacccgt ccgccactcg ttggcgacca aaatcaatca    420
ggtgcaagca ccatcaatca attgggccaa cgcgttcgac ttgcatgtat taggcacacc    480
gccggcgttc atcctgagcc aggatcaaan tctaa                               515
```

<210> SEQ ID NO 4
<211> LENGTH: 526
<212> TYPE: DNA
<213> ORGANISM: Lactobacillus reuteri
<220> FEATURE:
<221> NAME/KEY: misc_feature
<223> OTHER INFORMATION: deposited in the CECT under Accession No. 7266
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:

```
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (521)..(521)
<223> OTHER INFORMATION: n is a, c, g, or t

<400> SEQUENCE: 4
```

| | | | | | |
|---|---|---|---|---|---|
| accgngggnn | aacgacactg | cgngnacagn | ttactctcac | gcacgnttct | tctccaacaa | 60 |
| cagagcttta | cgagccgaaa | cccttcttca | ctcacgcggt | gttgctccat | caggcttgcg | 120 |
| cccattgtgg | aagattccct | actgctgcct | cccgtaggag | tatggaccgt | gtctcagttc | 180 |
| cattgtggcc | gatcagtctc | tcaactcggc | tatgcatcat | cgccttggta | agccgttacc | 240 |
| ttaccaacta | gctaatgcac | cgcaggtcca | tcccagagtg | atagccaaag | ccatctttca | 300 |
| aacaaaagcc | atgtggcttt | tgttgttatg | cggtattagc | atctgtttcc | aaatgttatc | 360 |
| ccccgctccg | gggcaggtta | cctacgtgtt | actcacccgt | ccgccactca | ctggtgatcc | 420 |
| atcgtcaatc | aggtgcaagc | accatcaatc | agttgggcca | gtgcgtacga | cttgcatgta | 480 |
| ttaggcacac | cgccggcgtt | catcctgagc | caggatcaaa | ntctaa | | 526 |

```
<210> SEQ ID NO 5
<211> LENGTH: 524
<212> TYPE: DNA
<213> ORGANISM: Lactobacillus reuteri
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (515)..(515)
<223> OTHER INFORMATION: n is a, c, g, or t

<400> SEQUENCE: 5
```

| | | | | | |
|---|---|---|---|---|---|
| gcntgggnga | acgtcactg | cggaacagtt | actctcacgc | acgttcttct | ccaacaacag | 60 |
| agctttacga | gccgaaaccc | ttcttcactc | acgcggtgtt | gctccatcag | gcttgcgccc | 120 |
| attgtggaag | attccctact | gctgcctccc | gtaggagtat | ggaccgtgtc | tcagttccat | 180 |
| tgtggccgat | cagtctctca | actcggctat | gcatcatcgc | cttggtaagc | cgttacctta | 240 |
| ccaactagct | aatgcaccgc | aggtccatcc | cagagtgata | gccaaagcca | tctttcaaac | 300 |
| aaaagccatg | tggcttttgt | tgttatgcgg | tattagcatc | tgtttccaaa | tgttatcccc | 360 |
| cgctccgggg | caggttacct | acgtgttact | cacccgtccg | ccactcactg | gtgatccatc | 420 |
| gtcaatcagg | tgcaagcacc | atcaatcagt | tgggccagtg | cgtacgactt | gcatgtatta | 480 |
| ggcacaccgc | cggcgttcat | cctgagncag | gatcnaaact | ctaa | | 524 |

```
<210> SEQ ID NO 6
<211> LENGTH: 519
<212> TYPE: DNA
<213> ORGANISM: Lactobacillus plantarum
<220> FEATURE:
```

<221> NAME/KEY: misc_feature
<222> LOCATION: (11)..(11)
<223> OTHER INFORMATION: n is a, c, g, or t

<400> SEQUENCE: 6

| | | | | | |
|---|---|---|---|---|---|
| ggcctgggaa | nccggtcata | cctggaacag | gttacctctc | agatatggtt | cttctttaac | 60 |
| aacagagttt | tacgagccga | aaccctttctt | cactcacgcg | gcgttgctcc | atcagacttt | 120 |
| cgtccattgt | ggaagattcc | ctactgctgc | ctcccgtagg | agtttgggcc | gtgtctcagt | 180 |
| cccaatgtgg | ccgattaccc | tctcaggtcg | gctacgtatc | attgccatgg | tgagccgtta | 240 |
| cctcaccatc | tagctaatac | gccgcgggac | catccaaaag | tgatagccga | agccatcttt | 300 |
| caaactcgga | ccatgcggtc | caagttgtta | tgcggtatta | gcatctgttt | ccaggtgtta | 360 |
| tccccgctt | ctgggcaggt | ttcccacgtg | ttactcacca | gttcgccact | cactcaaatg | 420 |
| taattcatga | tgcaagcacc | aatcattacc | agagttcgtt | cgacttgcat | gtattaggca | 480 |
| cgccgccagc | gttcgtcctg | agacaggatc | aaaactcta | | | 519 |

<210> SEQ ID NO 7
<211> LENGTH: 474
<212> TYPE: DNA
<213> ORGANISM: Enterococcus hirae

<400> SEQUENCE: 7

| | | | | | |
|---|---|---|---|---|---|
| gacagttact | ctcatccttg | ttcttctcta | acaacagagt | tttacgatcc | gaaaaccttc | 60 |
| ttcactcacg | cggcgttgct | cggtcagact | ttcgtccatt | gccgaagatt | ccctactgct | 120 |
| gcctcccgta | ggagtttggg | ccgtgtctca | gtcccaatgt | ggccgatcac | cctctcaggt | 180 |
| cggctatgca | tcgtcgcctt | ggtgagccgt | tacctcacca | actagctaat | gcaccgcggg | 240 |
| tccatccatc | agcgacaccc | gaaagcgcct | ttcaaatcaa | aaccatgcgg | tttcgattgt | 300 |
| tatacggtat | tagcacctgt | ttccaagtgt | tatcccctc | tgatgggcag | gttacccacg | 360 |
| tgttactcac | ccgttcgcca | ctcctctttt | tccggtggag | caagctccgg | tggaaaaga | 420 |
| agcgttcgac | ttgcatgtat | taggcacgcc | gccagcgttc | gtcctgagcc | aggt | 474 |

<210> SEQ ID NO 8
<211> LENGTH: 469
<212> TYPE: DNA
<213> ORGANISM: Lactobacillus plantarum

<400> SEQUENCE: 8

| | | | | | |
|---|---|---|---|---|---|
| ttactctcag | atatgttctt | ctttaacaac | agagttttac | gagccgaaac | ccttcttcac | 60 |
| tcacgcggcg | ttgctccatc | agactttcgt | ccattgtgga | agattcccta | ctgctgcctc | 120 |
| ccgtaggagt | ttgggccgtg | tctcagtccc | aatgtggccg | attaccctct | caggtcggct | 180 |
| acgtatcatt | gccatggtga | gccgttaccy | caccatctag | ctaatacgcc | gcgggaccat | 240 |
| ccaaaagtga | tagccgaagc | catctttcaa | gctcggacca | tgcggtccaa | gttgttatgc | 300 |
| ggtattagca | tctgtttcca | ggtgttatcc | cccgcttctg | ggcaggtttc | ccacgtgtta | 360 |
| ctcaccagtt | cgccactcac | tcaaatgtaa | atcatgatgc | aagcaccaat | caataccaga | 420 |
| gttcgttcga | cttgcatgta | ttaggcacgc | cgccagcgtt | cgtcctgag | | 469 |

<210> SEQ ID NO 9
<211> LENGTH: 493
<212> TYPE: DNA
<213> ORGANISM: Enterococcus faecalis

<400> SEQUENCE: 9

```
ctatcatgca agtcgaacgc ttctttcctc ccgagtgctt gcactcaatt ggaaagagga      60
gtggcggacg ggtgagtaac acgtgggtaa cctacccatc agaggggat aacacttgga      120 aacaggtgct aataccgcat aacagtttat gccgcatggc ataagagtga aaggcgcttt     180
cgggtgtcgc tgatggatgg acccgcggtg cattagctag ttggtgaggt aacggctcac     240
caaggccacg atgcatagcc gacctgagag ggtgatcggc cacactggga ctgagacacg     300
gcccagactc ctacgggagg cagcagtagg gaatcttcgg caatgacga aagtctgacc      360 gagcaacgcc gcgtgagtga agaaggtttt cggatcgtaa aactctgttg ttagagaaga     420
acaaggacgt tagtaactga acgtcccctg acggtatcta accagaaagc cacggctaac     480
tacgtgccca gca                                                        493
```

<210> SEQ ID NO 10
<211> LENGTH: 524
<212> TYPE: DNA
<213> ORGANISM: Lactobacillus salivarius
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t

<400> SEQUENCE: 10

```
gggtggggng ancagaacat gaaatgaaca gtttacatct cacctcgctg nttcttcctc    60
taacaacaga gcttttacga ctccgaagga ccttcttcac atcacgcggc gtntgctcca    120
tcagacttgc gtccattgtg gaagattccc tactgctgcc tcccgtagga gtttgggccg    180
tgtctcagtc ccaatgtggc cgatcaacct ctcagattcg gctacgtatc atcaccttgg    240
taggccgtta ccccaccaac tagttaatac gccgcgggtc catctaaaag cgatagnaga    300 accatcttc atctaaggat catgcgatcc ttagagatat acggnattag cacctgtttc     360
caagtgttat cccttctttt taggcaggtt acccacgtgt tactcacccg tccgccactc    420
aacttcttac ggtgaatgca agcattcggt gtaagaaagt ttcgttcgac ttgcatgtat    480
taggcacgcc gccagcgttc gtnatgagcc aggatcaaac tcta                     524
```

<210> SEQ ID NO 11
<211> LENGTH: 524
<212> TYPE: DNA
<213> ORGANISM: Lactobacillus reuteri
<220> FEATURE:
<221> NAME/KEY: misc_feature
<222> LOCATION: (3)..(3)

```
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (515)..(515)
<223> OTHER INFORMATION: n is a, c, g, or t

<400> SEQUENCE: 11
gcntgggnga acggtcactg cggaacagtt actctcacgc acgttcttct ccaacaacag        60
agctttacga gccgaaaccc ttcttcactc acgcggtgtt gctccatcag gcttgcgccc       120
attgtggaag attccctact gctgcctccc gtaggagtat ggaccgtgtc tcagttccat       180
tgtggccgat cagtctctca actcggctat gcatcatcgc cttggtaagc cgttacctta       240
ccaactagct aatgcaccgc aggtccatcc cagagtgata gccaaagcca tctttcaaac       300
aaaagccatg tggcttttgt tgttatgcgg tattagcatc tgtttccaaa tgttatcccc       360
cgctccgggg caggttacct acgtgttact cacccgtccg ccactcactg gtgatccatc       420
gtcaatcagg tgcaagcacc atcaatcagt tgggccagtg cgtacgactt gcatgtatta       480
ggcacaccgc cggcgttcat cctgagncag gatcnaaact ctaa                        524
```

MAMMALIAN MILK MICROORGANISMS, COMPOSITIONS CONTAINING THEM AND THEIR USE FOR THE TREATMENT OF MASTITIS

CROSS-REFERENCE TO RELATED APPLICATIONS

This application is filed under the provisions of 35 U.S.C. §371 and claims the priority of International Patent Application No. PCT/EP2008/056768 filed on 2 Jun. 2008 entitled "Mammalian Milk Microorganisms, Compositions Containing Them and Their Use for the Treatment of Mastitis" in the name of Rocío Martín Jiménez, et al., which claims priority of European Patent Application No. EP 07380158.1 filed on 31 May 2007, both of which are hereby incorporated by reference herein in their entirety.

FIELD OF THE INVENTION

The present invention relates to a novel approach to prevent or treat mastitis both in humans and animals through the use of mammalian milk-derived microorganisms obtained from healthy hosts of the homologous species; to those new probiotic microorganisms obtained from milk able to reduce infectious mastitis; to the use of these probiotic bacteria for the prophylaxis or treatment against mastitis and other diseases; and finally, to compositions comprising these compounds.

BACKGROUND OF THE INVENTION

Mastitis is an inflammation and infection of the mammary gland that is particularly frequent in women and other mammal females during lactation. Mastitis is mainly caused by staphylococci and/or streptococci selection and overgrowth in the mammary ducts and mammary areola glands. Human mastitis affects up to 30% of lactating women and often leads to a precocious and undesired weaning because it is a really painful condition.

Moreover, mastitis is not human-specific pathology but affects to all mammalian species. In this sense, infectious mastitis in animal species and breeds reared for milk production, such as cows, ewes or goats, is an important economic problem since milk produced during the infective process must be discarded due to the high bacterial and somatic cells counts. In addition, mastitis can be an important problem in those domestic species (pigs, rabbits . . . ) and breeds (e.g., meat-producing bovine) not dedicated to milk production since a reduced milk supply of low bacteriological quality may notably increase the morbidity and mortality rates among the offspring.

In these cases, antibiotic-based therapy has emerged as the unique therapeutical option. However, current wide-spectrum or Gram positive-targeted antibiotics are poorly effective for the staphylococcal and streptococcal strains causing mastitis and, in fact, such treatments can be in some circumstances, detrimental because they usually eliminate the commensal flora that characterise mammal milk, which could exert some protective effects. Moreover, antibiotic therapy may result in the appearance of antibiotic residues in the milk, which is also detrimental if occurring during the lactating period. Alternatively, recombinant bovine GM-CSF has also been used for the treatment of subclinical mastitis caused by *S. aureus* (Takahashi, H. et al. 2004, Cad. J. Vet. Res. 68:182-187) but did not prove efficient in the treatment of late-stage *S. aureus* infection.

An alternative approach for the treatment of mastitis is the use of probiotics. For instance, Sytnik, S. I. et al. (Vrach Delo., 1990, 3:98-100) attempted to use *Bifidobacteriumi* for preventing mastitis but did not observe any inhibition in the residence time of the breast microflora. Greene, W. A. et al. (J. Dairy Sci., 1991, 74:2976-2981) described the use of a commercial *lactobacillus* preparation for the treatment of elevated somatic cell count (SSC) when administered by direct intramammary injection but conclude that the *Lactobacillus* product used in the assay was not effective as an intramammary treatment of subclinical mastitis based on SCC. The U.S. Pat. No. 4,591,499 describes a method for treating mastitis using an intramammary injection of an oil in water emulsion containing a non-pathogenic *lactobacillus* strain or a mixture of strains. However, the strains described in this document appear to act by means of a non-specific decrease in the pH in the mammary gland and, due to their particular formulation as emulsions, need to be administered by direct intramammary injection. The Russian patent RU2134583 describes the use of topic composition containing lactobacterin (microbe mass of lactobacteria that have been live lyophilized/dried in culture medium) or bifidumbacterin (a lyophilised biopreparation immobilized on special activated charcoal) for the treatment of massive microbe dissemination of breast milk. However, this preparation is only suitable for the topic administration and forms part of a multi-step treatment that includes relaxation massage and application of a suspension of organisms derived from the normal microflora of the intestine additionally containing a protective film-forming medium. The international patent application WO05/34970 describes the treatment of mastitis by direct intramammary injection of a *Lactococcus lactis* strain.

Therefore, all the prior art described above relate to the use of probiotic strains by either intramammary injection or topical application. Thus, there is a desire in the art for additional approaches to allow the prevention and treatment of mastitis and other mammary gland pathologies, in women and in other mammal females, which can be more easily applied and by less invasive means.

SUMMARY OF THE INVENTION

The present invention is based on the unexpected and surprising finding that mammalian milk contains probiotic strains that are able to be transferred to the mammary gland after their oral intake, and exert a therapeutic effect locally against the pathogens that cause mastitis, thus helping to reduce the incidence of mastitis. Moreover, these strains have a number of additional unexpected advantageous properties which make them useful for the treatment of other diseases. The present invention is advantageous with respect to the methods known in the art in view of the valuable properties that lactation may provide, and due to the economic interest of milk productivity to farmers.

In a first aspect, the invention provides a process for the selection of probiotics comprising the steps of:
(i) isolating lactic acid bacteria or bifidobacteria strains present in the fresh milk from a mammalian species by selection in lactic acid culture media,
(ii) selecting those strains from step (i) that are capable of being transferred to the mammary gland after oral intake and/or colonise the mammary gland after its topic application,
(iii) selecting those strains from step (ii) which are able to reduce the rates of survival and/or the rates of adhesion to epithelial cells of *Staphylococcus aureus* and (iv) selecting those strains from step (iii) that are capable of protecting animals from mastitis.

In another aspect, the invention provides probiotic strains obtainable by the process of the invention.

In another aspect, the invention provides a supernatant of a culture of a strain or of a mixture of strains according to the invention.

In a further aspect, the invention provides a composition, a pharmaceutical product, a feed or a nutritional product comprising at least a probiotic strain of the invention or a supernatant of a culture of one or more strains of the invention.

In another aspect, the invention provides the use of the probiotic strains of the invention or the culture supernatant for the manufacture of a medicament for the treatment and/or prophylaxis of a chronic or acute infection or infestation, or of an undesirable microbial colonization, wherein the infection, infestation or colonization is caused by parasites, bacteria, yeast, fungi or viruses, affecting any body surface or mucosa in a subject or animal in need thereof.

In a further aspect, the invention provides the use of a probiotic strain or of a mixture of probiotic strains of the invention or the culture supernatant for the manufacture of a medicament for the treatment and/or prophylaxis of hypersensitivity reactions to food and metabolic intolerance; of constipation and other gastro-intestinal disorders; of inflammatory or auto-immune disorders selected from the group of IBD, ulcerative colitis, arthritis, atherosclerosis, multiple sclerosis, psoriasis or sarcoidosis; and of tumour growth, metastasis and cancer in subject or animal in need thereof.

In a further aspect, the invention provides the use of a probiotic strain or of a mixture of probiotic strains or the culture supernatant of the invention for the manufacture of a medicament for the treatment and/or prophylaxis of allergic disorders and asthma in a subject or animal in need thereof.

In a further aspect, the invention provides the use of a probiotic strain or of a mixture of probiotic strains or the culture supernatant of the invention for the manufacture of a medicament for the treatment and/or prophylaxis of temporally depressed immune levels in individuals or animals subjected to physiological and management-derived stress.

BRIEF DESCRIPTION OF THE FIGURES

FIG. 1 provides the sequences of the 16S rRNA sequences of the probiotic strains bacteria included in this invention and their PCR-RAPD profile.

FIG. 7 shows the effect of the probiotic strains on a model of orally-induced Salmonella infection. A) Graph bar showing the effect of probiotic treatment in the inhibition of Salmonella translocation to the spleen. The number of Salmonella colonies was measured in the spleens of mice treated with the probiotics, with (grey bars) or without vaccination (black bars) with $10^8$ cfu of inactivated Salmonella, after 24 hour of an oral challenge with $10^{10}$ cfu Salmonella. B) Survival curves of the animals after Salmonella infection.

FIGS. 9A and 9B correspond to the funentation pattern of the different probiotic strains of the invention, wherein positive fermentable substrates are indicated in grey.

DETAILED DESCRIPTION OF THE INVENTION

Figure 2:
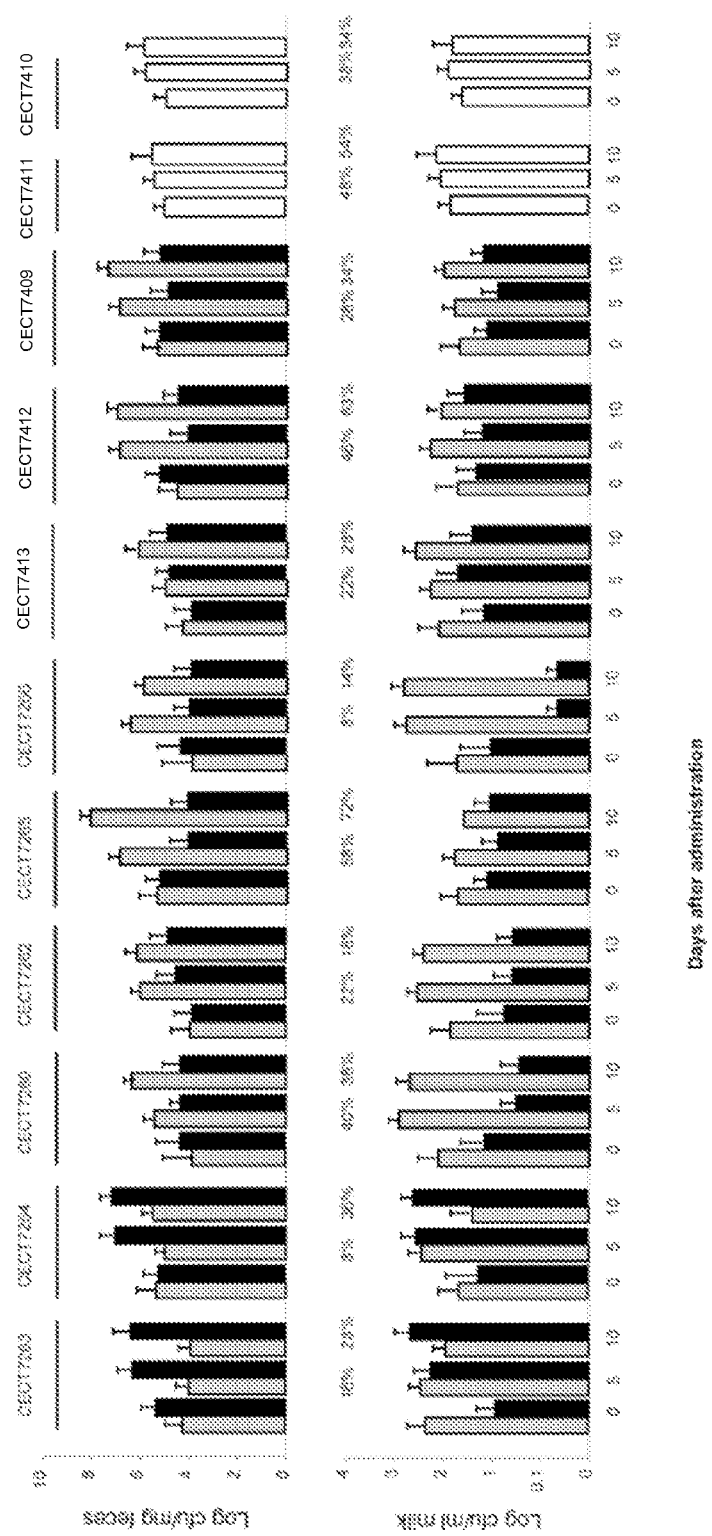
FIG. 2 is a graph bar showing the transfer ability to the mammary gland of and the gut colonization by the strains of the present invention in mice. The number of lactobacilli (grey bars), bifidobacteria (black bars) and enterococcus (white bars) in expressed milk and fecal samples in lactating mice supplemented daily for 14 days with $10^8$ cfu of the genetically-labeled strains was analyzed by bacterial colony plating. Milk and fecal samples were collected at day 0, 5 and 10 of probiotic supplementation. PCR-positive colonies in milk are indicated as %.

The invention provides a new method for the prophylactic and therapeutic treatment of infectious mastitis both in women and other mammal females in need thereof. The method is based in the use of specific probiotic strains specially selected for that particular application.

In a first aspect, the invention provides a process for the selection of probiotics comprising the steps of:
(i) isolating lactic acid bacteria or bifidobacteria strains present in the fresh milk from a mammalian species by selection in lactic acid culture media,
(ii) selecting those strains from step (i) that are capable of being transferred to the mammary gland after oral intake and/or colonise the mammary gland after its topic application,
(iii) selecting those strains from step (ii) which are able to reduce the rates of survival and/or the rates of adhesion to epithelial cells of Staphylococcus aureus and
(iv) selecting those strains from step (iii) that are capable of protecting animals from mastitis.

In step (i), any milk obtained from a mammalian organism can be used as starting material for the process of the invention. In a preferred embodiment, the milk used is human, bovine, porcine, sheep, cat or canine milk. Moreover, any lactic acid culture media known in the art can be used for selecting the strains. Preferably, the lactic acid culture media is selected from MRS medium, APT medium, RCM medium, LM17 medium, GM17 medium and Elliker medium. Most preferably, the lactic acid culture media is MRS medium.

In step (ii), the strains isolated in step (i) are selected based on their ability to being transferred to the mammary gland after oral intake and/or colonise the mammary gland after topic application. For detecting the ability to being transferred to the mammary gland, an assay such as described in WO2004003235 for detecting transfer of a microorganism to the milk after oral intake can be used.

In step (iii), any assay known in the art for measuring survival rates of Staphylococcus and for measuring adhesion rates of S. aureus to epithelial cells can be used. In a preferred embodiment, the effect of the probiotics in the adhesion rates is measured using a confluent culture of an intestinal cell line to which the S. aureus cells and the probiotics of the invention are added and the number of attached S. aureus cells is measured by any suitable technique. Typically, the intestinal cell line is Caco-2 and the number of attached cells is measured by direct inspection of the cell mono layers under light microscopy. Moreover, the selection step (iii) may also or alternatively involve measuring the viability of viability of S. aureus in the presence of the probiotic strains. Any assay suitable for measuring growth inhibition of bacterial strains may be used. Typically, the assessment of S. aureus viability is carried out by an agar well diffusion assay.

In step (iv), any assay to measure protection of mastitis can be used. Preferably, the assay involves using an animal model of mastitis wherein at least one of the pathogens known to be the causative agent of mastitis is injected into the mammary gland. More preferably, the animal model is a mouse and the pathogen that needs to be administered to cause mastitis is S. aureus.

In another aspect, the invention provides a probiotic strain which is obtainable by the process of the invention. Preferably, the probiotic strain is selected from the group of Bifidobacterium breve deposited in the CECT under Accession No 7263, Bifidobacterium breve deposited in the CECT under Accession No 7264, Lactobacillus reuteri deposited in the CECT under Accession No 7260, Lactobacillus plantarum deposited in the CECT under Accession No 7262, Lactobacillus fermentum in the CECT under Accession No 7265, Lactobacillus reuteri deposited in the CECT under Accession No 7266, Lactobacillus salivarius in the CECT under Accession No 7409, Enterococcus hirae in the CECT under Accession No 7410, Enterococcus faecalis in the CECT under Accession No 7411, Lactobacillus plantarum in the CECT under Accession No 7412, Lactobacillus reuteri in the CECT under Accession No 7413.

In a further aspect, the invention provides a supernatant of a culture of one or more of the strains according to the invention. The supernatant can be obtained from the culture by any means available to the skilled person, including centrifugation, filtration, flotation and the like.

In a further aspect, the invention provides a probiotic strain or a mixture of probiotic strains according of the invention or a supernatant of a culture of one or more of the strains according to the invention for use as a medicament.

In another aspect, the invention provides a composition which comprises at least one of the bacterial strains of the invention. Preferably, the composition comprises at least 2, at least 3, at least 4, at least 5 or at least 6 of the strains of the invention, and wherein each of the strains is represented in the composition in a proportion from 0.1% to 99.9%, preferably from 1% to 99%, more preferably from 10% to 90%. In another embodiment, the composition comprises any of the bacterial strains of the invention together with another strain or mixture of strains and where each of the strains is represented in the composition in a proportion from 0.1% to 99.9%, preferably from 1% to 99%, more preferably from 10% to 90%. In another aspect, the invention provides a composition which comprises a supernatant of a culture of one or more of the strains according to the invention. Preferably, the supernatant is represented in the composition in a proportion from 0.1% to 99.9%, more preferably from 1% to 99% and even more preferably from 10% to 90%.

In another aspect, the invention provides a pharmaceutical composition comprising a therapeutically effective amount of at least one strain or a composition of the invention or of a supernatant of a culture of one or more of the strains according to the invention. The pharmaceutical preparation can take the form of tablets, capsules, liquid bacterial suspensions, dried oral supplements, wet oral supplements, dry tube feeding or a wet tube feeding. Preferably the probiotic, the probiotic-containing or supernatant-containing composition and pharmaceutical product is directed to the oral, gastric and/or to the intestinal mucosal surface; however, it could also be directed to naso-pharingeal, respiratory, reproductive or glandular mucosa, and/or to the mammary gland and it could be administered to women and animals by an oral, nasal, ocular, rectal, topical and/or vaginal route.

In another aspect, the invention provides a feed or a nutritional product comprising at least a probiotic strain according to the invention or of a supernatant of a culture of one or more of the strains according to the invention. Non-limiting examples of suitable foodstuffs which can be used in the present invention are milk, yoghourt, cheese, curd, fermented milks, milk based fermented products, fermented cereal based products, fermented meat products, other milk based or cereal based powders, clinical nutrition formula, ice-creams, juices, bread, cakes or candies, animal feed formulations, semi- or synthetic diet formulations, infant formulae, clinical nutrition formulae, ice-creams, juices, flours, bread, cakes, candies or chewing-gums.

The required dosage amount of the probiotic strains in the composition, food or pharmaceutical composition described before will vary according to the nature of the disorder or the proposed use of the composition, whether used prophylactically or therapeutically and the type of organism involved.

Any suitable dosage of the probiotics or combinations thereof may be used in the present invention provided that the toxic effects do not exceed the therapeutic effects.

Therapeutic efficacy and toxicity may be determined by standard pharmaceutical procedures with experimental animals, such as by calculating the $ED$, (the dose therapeutically effective in 50% of the population) or $LD$ (the dose lethal to 50% of the population) statistics. The dose ratio of toxic to therapeutic effects is the therapeutic index, which can be expressed as the $LD/ED$ ratio. Nevertheless, the activity of the new microorganisms in the individual is naturally dose dependent. That is, the more the novel microorganisms are incorporated by means of ingesting or administration of the above food material or the pharmaceutical composition, the higher protective and/or therapeutic activity of the microorganisms. Since the microorganisms of this invention are not detrimental to mankind and animals and have eventually been isolated from healthy human breast milk, a high amount thereof may be incorporated so that essentially a high proportion of the individual's mucosa will be colonized by the novel microorganisms. Compositions which exhibit large therapeutic indices are preferred. The data obtained from animal studies are used to formulate a range of dosage for human or animal use. The dosage contained in such compositions is preferably within a range of circulating concentrations that includes the ED, with little or no toxicity. The dosage varies within this range depending upon the dosage form employed, the sensitivity of the patient, and the route of administration. The exact dosage will be determined by the practitioner, in light of factors related to the subject requiring treatment. For instance, for preparing a food composition according to the present invention at least one of the probiotic strains of the present invention is incorporated in a suitable support, in an amount of from $10^5$ cfu/g to about $10^{12}$ cfu/g support material, preferably from about $10^6$ cfu/g to about $10^{11}$ cfu/g support material, more preferably from about $10^6$ cfu/g to about $10^{10}$ cfu/g support material.

In the case of a pharmaceutical composition, the dosage of the probiotic strain should be from about $10^5$ cfu/g to about $10^{14}$ cfu/g support material, preferably from about $10^6$ cfu/g to about $10^{13}$ cfu/g support material, more preferably from about $10^7$ cfu/g to about $10^{12}$ cfu/g support material. For the purpose of the present invention the abbreviation cfu shall designate a "colony forming unit" that is defined as the number of bacterial cells as revealed by microbiological counts on agar plates.

Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting compositions may be administered every 3 to 4 days, every week, or biweekly depending on the half-life and clearance rate of the particular formulation.

In a preferred embodiment, the invention also refers to compositions of the strains of this invention in a lyophilized, freeze dried or dried form, which can be obtained by any conventional method known in the art.

In another aspect, the invention provides a composition, pharmaceutical product, feed or nutritional product wherein the probiotic strain or the mixture thereof is in a partially or totally inactivated form.

Many people have a disturbed intestinal microflora, that is, the balance between useful and harmful intestinal bacteria is disturbed. A number of factors, among others stress, the presence of bile salts, and specially diet, influence the bacterial flora. In these situations the fermentation process could be disturbed and the number of useful bacteria be reduced, with the consequence that the colon mucosa withers away and ceases to function at the same time as the potentially malignant bacteria rapidly grow in number. The probiotic strains of the invention are capable of preventing adhesion of S. aureus to epithelial cells, as well as of reducing survival rates of S. aureus cells and of many other pathogens. Thus, the probiotic strains of the invention are particularly useful for the treatment of said diseases since they contribute effectively to the killing of the pathogens while at the same time; they contribute to the repopulation of the mucosal surface with the physiological microflora.

For this reason, one aspect of this invention is the use of probiotics of the invention and of the supernatants of a culture of one or more strains of the invention for the preparation of a pharmaceutical composition for the prophylactic or therapeutic treatment of chronic or acute infection, or infestation or of undesirable microbial colonization, of a mucosal surface or any other human location, wherein the infection, infestation or colonization is caused by parasites, bacteria, yeast, fungi or viruses, affecting any body surface or mucosa, said therapeutic treatment comprising the administration of an effective amount of a probiotic, or a probiotic-containing composition, to a subject in need thereof. In a preferred embodiment, the infection or colonization is caused by parasites, bacteria, yeast, fungi or viruses, of any body surface or mucosa in a subject or animal in need thereof.

The probiotics of the invention have been selected based on their ability to colonise the mammary gland after oral intake and to prevent adhesion to epithelial cells and to decrease survival of S. aureus. Thus, the strains are suitable for treatment of mastitis. Accordingly, in a further aspect, the invention provides the use of the probiotic strains of the inventions and of the supernatants of a culture of one or more strains of the invention for the preparation of a pharmaceutical composition for the treatment or prophylaxis of human and animal infectious mastitis. This process consists in the use of probiotic strains selected from homologous fresh milk and in the ability of these strains to be transferred to the mammary gland and exert there their benefits, such as the inhibition of the staphylococcal infection.

Moreover, the probiotic strains of the invention have also been shown to possess some of the characteristics attributed to a potential probiotic strain, namely safety and good resistance to digestion process and the ability of gut colonization. Therefore, the strains are capable of reaching the intestinal tract after oral intake and exert their therapeutic properties there. Accordingly, in a preferred embodiment, the invention provides the use of the probiotic strains of the invention and of the supernatant of a culture of one or more of the strains of the invention for the preparation of a pharmaceutical composition for the treatment of neonatal diarrhoea.

The probiotic strains are known to reduce the production of pro-inflammatory cytokines by activated macrophages during chronic inflammatory disorders. Accordingly, in another aspect, the invention provides the use of the bacterial strains, compositions of the invention and supernatants of a culture of one or more strains of the invention for the preparation of a pharmaceutical composition for the manufacture of a medicament for the treatment of inflammatory or auto-immune disorders. Non-limiting examples of such inflammatory and autoimmune diseases include IBD, ulcerative colitis, arthritis, atherosclerosis, multiple sclerosis, psoriasis or sarcoidosis.

The probiotic strains according to the invention are capable of repopulating the immune gut barrier after oral intake and thus, they are also particularly suitable for the improvement of the immune gut barrier in a subject or animal in need thereof. Accordingly, in another aspect, the invention provides the use of one or more probiotic strains of the invention and of the supernatants of a culture of one or more strains of the invention for the preparation of a pharmaceutical composition for the preparation of a medicament for the treatment and/or prophylaxis of hypersensitivity reactions to food and metabolic intolerance such as lactose intolerance; of constipation and other gastro-intestinal disorders.

Probiotics are known to be useful for counteracting cancer due to their effects in the inhibition of carcinogenic toxins in the intestines such as nitrosamines but also for the effect of this probiotics in the modulation of the natural immune response. Accordingly, in a further aspect, the invention provides the use of the strains stated in this invention and of the supernatants of a culture of one or more strains of the invention for the preparation of a pharmaceutical composition for the prophylactic or therapeutic treatment of some cancer types and for inhibiting tumor growth, metastasis and cancer in subject or animal in need thereof.

The strains of the invention are capable of modulating the immune response and the balance between Th1 and Th2 cytokines Accordingly, in a further aspect, the invention provides the use of the strain, compositions and supernatants of the invention in the manufacture of a medicament for the treatment and/or prophylaxis of allergic disorders, asthma and disorders related with the development of tolerance against ingested proteins.

In a further aspect, the invention provides the use of the strains, compositions and supernatant of the invention in the manufacture of a medicament for the treatment and/or prophylaxis of temporally depressed immune levels in individuals such as produced during aging or in healthy individuals who are subject to intense exertion or in general to a great physiological strain or stress.

In another aspect, the invention provides for the therapeutic use of the probiotic strain, of the combinations of strains and of the supernatants wherein the strain or strains are administered via oral, topic, nasal, enteral, ocular, urogenital, rectal or vaginal.

Moreover, due to the presence of the selected strains in breast milk, the subjects in need of treatment could be not only those who intake directly the selected strains but also the fetus or breast feeding babies. Accordingly, in still a further aspect, the invention provides the use of the strains, compositions and supernatant of the invention in the manufacture of a medicament designed to be administered to lactating woman for the therapeutic or prophylactic treatment of their fetus and/or their breastfed babies.

The following methods and examples illustrate the invention.

EXAMPLES

Example 1

Isolation of Probiotics from Mammal Milk

Fresh milk samples (2 ml except in the case of the bitches where only 0.5 ml were collected) were obtained from 23 healthy women at day 6-14 after labour; 8 sows at day 5 after labour, 9 bitches at day 2-10 after labour and 4 cows at day 2 after labour.

Neither the women nor the animals had complications during labour and no antibiotic therapy was administered in the last two weeks prior milk sample collection. All milk samples were immediately frozen at −80° C.

In order to isolate bacterial strains from these samples, serial dilutions of 0.1 ml in peptone water were platted on MRS, APT, RCM, LM17, GM17 and Elliker agar plates at 37° C. in both aerobic and anaerobic conditions for 24-48 hours. Among the approx. 1200 colonies initially obtained, 120 (10%; include representatives of the different morphologies observed on the plates) were selected and subcultured in MRS agar at 37° C. in anaerobic conditions. Among them, we further selected 68 isolates with the following characteristics: non-spore-forming, catalase- and oxidase-negative Gram-positive rods.

These 68 selected isolates were further characterized both phenotipically (API CH50, APIZYM and antibiotic resistance evaluation) and genetically (16S rRNA sequencing and RAPD-PCR profile). This characterization resulted in 59 different bacterial strains which were further evaluated through the screening process described in this invention in order to obtain potential probiotic candidates to be able to protect against mastitis.

After this screening process, only 6 strains (2 from women, 2 from bitches and 2 from sows) fulfilled all the defined criteria. Other lactic acid bacteria strains were obtained from other mammal species, such as goat, ewe, cat, rat and mice, but they were not successful to fulfil all the screening criteria and for this reason they are not included in this invention.

Bifidobacterium breve said bacteria being obtained from human milk
Bifidobacterium breve said bacteria being obtained from human milk
Lactobacillus reuteri said bacteria being obtained from porcine milk
Lactobacillus plantarum said bacteria being obtained from porcine milk
Lactobacillus reuteri said bacteria being obtained from canine milk
Lactobacillus fermentum said bacteria being obtained from canine milk
Lactobacillus salivarius said bacteria being obtained from porcine milk
Enterococcus hirae said bacteria being obtained from feline milk
Enterococcus faecalis said bacteria being obtained from feline milk
Lactobacillus plantarum said bacteria being obtained from feline milk
Lactobacillus reuteri said bacteria being obtained from canine milk Example 2

Physiologic and Genetic Characterization

All these isolates were physiological and genetically characterized. For the identification of each probiotic strain, we performed a fermentation API 50CH (BioMerieux) analysis of the strains at 37° C. in anaerobic conditions for 24 and 48 hours, following the manufacturer instructions. The 24 hours results were summarized in Table I. A positive fermentable substrate is that with a value higher than 3.

Due to the low specificity of the API characterization, we also performed the analysis of the 16S rRNA sequences of the selected bacterial strains. The 16S RNA sequence of the selected bacteria and their RAPD-PCR profile are shown in FIG. 1. The results obtained led to the classification of the bacterial strains as indicated above. With this classification the bacterial strains of the invention were deposited according to the Budapest Agreement at the CECT—Colección Espanõla de Cultivos Tipo—, Valencia (Spain) on Apr. 17, 2007 and accorded the following accession numbers:
Bifidobacterium breve CECT7263
Bifidobacterium breve CECT7264
Lactobacillus reuteri CECT7260
Lactobacillus plantarum CECT7262
Lactobacillus fermentum CECT7265
Lactobacillus reuteri CECT7266

The following bacterial strains of the invention were deposited according to the Budapest Agreement at the CECT—Colección Espanõla de Cultivos Tipo—, Valencia (Spain) on May 30, 2008
Lactobacillus salivarius CECT 7409
Enterococcus hirae CECT 7410
Enterococcus faecalis CECT 7411
Lactobacillus plantarum CECT 7412
Lactobacillus reuteri CECT 7413

TABLE I

Fermentation pattern of the different probiotic strains of the invention
Positive fermentable substrates are indicated in grey.

| TEST | 7263 | 7264 | 7260 | 7262 | 7265 | 7266 | 7413 | 7412 | 7409 | 7411 | 7410 |
|---|---|---|---|---|---|---|---|---|---|---|---|
| Glycerol | 0 | 0 | 0 | 0 | 0 | 0 | 0 | 0 | 0 | 0 | 0 |
| Erythritol | 0 | 0 | 0 | 0 | 0 | 0 | 1 | 0 | 0 | 0 | 0 |
| D-Arabinose | 0 | 0 | 0 | 0 | 0 | 0 | 5 | 0 | 0 | 5 | 5 |
| L-Arabinose | 0 | 0 | 0 | 5 | 0 | 5 | 5 | 5 | 0 | 1 | 0 |
| Ribose | 5 | 0 | 0 | 5 | 5 | 5 | 5 | 5 | 4 | 0 | 0 |
| D-Xylose | 0 | 0 | 0 | 0 | 0 | 5 | 0 | 0 | 0 | 0 | 0 |
| L-Xylose | 0 | 0 | 0 | 0 | 0 | 0 | 0 | 0 | 0 | 5 | 5 |
| Adonitol | 0 | 0 | 0 | 0 | 0 | 0 | 5 | 0 | 0 | 5 | 5 |
| ☐ Methyl-xyloside | 0 | 0 | 0 | 0 | 0 | 5 | 5 | 0 | 0 | 5 | 5 |
| Galoctose | 5 | 5 | 5 | 5 | 5 | 5 | 5 | 5 | 5 | 5 | 5 |
| D-Glucose | 5 | 5 | 5 | 5 | 5 | 5 | 0 | 5 | 5 | 0 | 0 |
| D-Fructose | 5 | 5 | 0 | 5 | 5 | 0 | 5 | 5 | 5 | 0 | 0 |
| D-Mannose | 1 | 0 | 0 | 5 | 5 | 0 | 0 | 5 | 5 | 0 | 0 |
| L-Sorbose | 0 | 0 | 0 | 0 | 0 | 0 | 0 | 0 | 0 | 5 | 0 |
| Rhamnose | 0 | 0 | 0 | 0 | 0 | 0 | 0 | 0 | 0 | 5 | 0 |
| Dutcitol | 0 | 0 | 0 | 0 | 0 | 0 | 0 | 0 | 0 | 0 | 0 |
| Inositol | 0 | 0 | 0 | 0 | 0 | 0 | 0 | 0 | 0 | 0 | 0 |
| Mannitol | 4 | 0 | 0 | 5 | 5 | 0 | 4 | 5 | 5 | 5 | 5 |
| Sorbitol | 5 | 0 | 0 | 5 | 0 | 0 | 0 | 5 | 5 | 5 | 5 |
| ☐ Methyl-D-mannoside | 0 | 0 | 0 | 0 | 0 | 0 | 0 | 0 | 0 | 0 | 5 |
| ☐ Methyl-D-glucoside | 2 | 0 | 0 | 0 | 5 | 0 | 5 | 0 | 0 | 5 | 5 |
| N Acethyl glucosamine | 2 | 1 | 0 | 5 | 5 | 0 | 5 | 5 | 5 | 5 | 5 |
| Amygdaline | 0 | 1 | 0 | 5 | 0 | 0 | 5 | 5 | 0 | 5 | 5 |
| Arbutine | 0 | 0 | 0 | 5 | 0 | 0 | 5 | 5 | 4 | 5 | 5 |
| Esculine | 5 | 5 | 0 | 5 | 0 | 0 | 0 | 5 | 5 | 5 | 5 |
| Salicine | 1 | 0 | 0 | 5 | 0 | 0 | 5 | 5 | 0 | 0 | 5 |
| Celiobiose | 5 | 0 | 0 | 5 | 0 | 0 | 5 | 5 | 4 | 5 | 5 |
| Maltose | 5 | 5 | 5 | 5 | 5 | 5 | 5 | 5 | 5 | 5 | 5 |
| Lactose | 5 | 0 | 5 | 5 | 5 | 5 | 5 | 5 | 5 | 0 | 0 |
| Melibiose | 5 | 5 | 5 | 5 | 5 | 5 | 5 | 5 | 5 | 5 | 0 |
| Saccherose | 5 | 0 | 5 | 0 | 5 | 5 | 5 | 0 | 5 | 0 | 0 |
| Trehalose | 0 | 0 | 0 | 5 | 0 | 0 | 0 | 5 | 5 | 1 | 5 |
| Inuline | 0 | 0 | 0 | 0 | 0 | 0 | 0 | 0 | 0 | 0 | 0 |
| Melezitose | 0 | 0 | 0 | 0 | 0 | 0 | 5 | 0 | 0 | 0 | 0 |
| D-Raffinose | 5 | 0 | 5 | 5 | 5 | 5 | 0 | 5 | 5 | 0 | 0 |

TABLE I-continued

Fermentation pattern of the different probiotic strains of the invention
Positive fermentable substrates are indicated in grey.

| Substrate | 1 | 2 | 3 | 4 | 5 | 6 | 7 | 8 | 9 | 10 | 11 |
|---|---|---|---|---|---|---|---|---|---|---|---|
| Amidon | 5 | 0 | 0 | 0 | 0 | 0 | 0 | 0 | 0 | 0 | 0 |
| Glycogene | 5 | 4 | 0 | 0 | 0 | 0 | 0 | 0 | 0 | 5 | 0 |
| Xylitol | 0 | 0 | 0 | 0 | 0 | 0 | 5 | 0 | 0 | 0 | 0 |
| ☐ Gentiobiose | 0 | 2 | 0 | 5 | 0 | 0 | 0 | 5 | 0 | 0 | 0 |
| D-Turanose | 5 | 4 | 0 | 5 | 0 | 0 | 0 | 5 | 0 | 0 | 0 |
| D-Lyxose | 0 | 0 | 0 | 0 | 0 | 0 | 5 | 0 | 0 | 0 | 0 |
| D-Tagatose | 0 | 0 | 0 | 0 | 0 | 0 | 0 | 0 | 0 | 5 | 0 |
| D-Fucose | 0 | 0 | 0 | 0 | 0 | 0 | 0 | 0 | 0 | 1 | 0 |
| L-Fucose | 0 | 0 | 0 | 0 | 0 | 0 | 0 | 0 | 0 | 0 | 0 |
| D-Arabitol | 0 | 0 | 0 | 0 | 0 | 0 | 0 | 0 | 0 | 0 | 0 |
| L-Arabitol | 0 | 0 | 0 | 0 | 0 | 0 | 0 | 0 | 0 | 0 | 0 |
| Gluconate | 0 | 0 | 0 | 0 | 0 | 0 | 0 | 0 | 0 | 0 | 0 |
| 2 ceto-gluconate | 0 | 0 | 0 | 0 | 0 | 0 | 0 | 0 | 0 | 0 | 0 |
| 5 ceto-gluconate | 0 | 0 | 0 | 0 | 0 | 0 | 0 | 0 | 0 | 0 | 0 |

Example 3

Selective Screening of the Strains

Example 3a

Transfer to the Mammary Gland after Oral Intake

Once the different candidate strains were obtained from mammal milk as indicated in the first selection criteria, the following step in the selection process described in the present invention is that bacteria should be able to be transferred to milk after oral intake or topic application. In order to test this capability, the putative strains were genetically labelled as described previously (WO 2004/003235) and orally administered to pregnant rats as animal model. Total lactobacilli, bifidobacteria and enterococcus were measured in milk and neonatal fecal samples. Moreover, specific transfer of bacteria was analyzed by PCR screening of the colonies obtained from the milk of lactating rats and from the neonatal faeces.

Four pregnant Wistar rats were orally inoculated with $10^8$ cfu of genetically-labelled strains vehiculated in 0.5 ml of milk every two days from two weeks before labor. After labor, the transfer of genetically labelled bacteria to breast milk was analyzed by comparison of the bacteria isolated from the neonatal faeces at day 0, 5 and 10 after labor. All the plates were incubated for 24 hours at 37° C. under anaerobic conditions. For each sample obtained, total bifidobacteria, lactobacilli and enterococcus counts were measured. Among the colonies that grew on MRS plates, 50 were randomly selected from each sample and subcultured on Cm-MRS plates. Finally, the Cm-resistant colonies were used as templates to detect the specific genetic label colonies (FIG. 2). Transfer was considered positive when at least 1% of the colonies obtained were PCR-positive.

Example 3b

Inhibition of *Staphylococcus aureus* Survival

Figure 3:
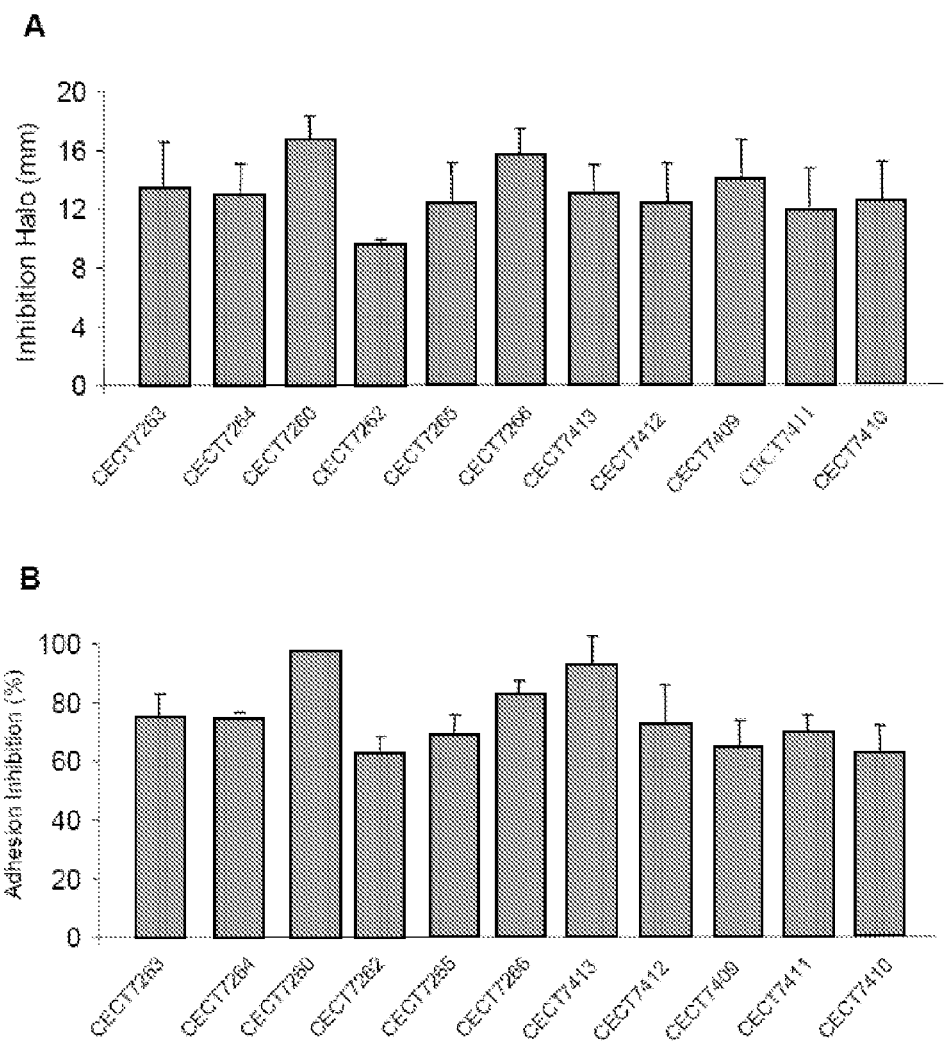
FIG. 3 is a graph bar showing the inhibition of the staphylococcal survival and adhesion produced after co-culture of the staphylococci with the strains included in this invention. A) The inhibitory effect of the probiotics included in this invention on Staphylococcus aureus survival was assessed in vitro by an agar well diffusion assay in TSA plates. The diameter of the inhibition halo (in millimetres) caused by the bacterial supernatants determines the antimicrobial effect. B) The adhesion of the pathogenic Staphylococcus aureus strain to Caco-2 cells was assessed in the presence of the probiotic strains of this invention. Ten randomized fields were counted and the results expressed as the mean of the % of adhered gram-negative bacteria attached to the cells compared to the number of pathogenic bacteria adhered in absence of probiotics.

The probiotic strains of this invention were assessed for their capability to produce bactericidal metabolites able to reduce the survival of *Staphylococcus aureus* using an agar well diffusion assay. TSA agar plates containing $10^6$ cfu/ml of *S. aureus* were prepared. Wells with a diameter of 5 mm where cut in the agar using a sterile cork-borer. Then, 50 μl of a 2-fold concentrated supernatant of each probiotic strain solution were added to the wells and allowed to diffuse into the agar during a 2 hours preincubation period at 4° C., followed by aerobic incubation of the plates at 37° C. for 16-18 hours. After the incubation period, an inhibitory halo was observed and measured (in millimetres) to evaluate the bactericide effect of the probiotic candidates (FIG. 3A).

Example 3c

Inhibition of *Staphylococcus aureus* Adhesion to Epithelial Cells

Caco-2 intestinal cell lines were cultured to confluence in 35 mm plastic dishes containing 2 ml medium without antibiotics. On day 10-14 post-confluence, 1 ml of media was replaced with 1 ml of a suspension of $10^8$ probiotic bacteria in DMEM. The cultures were incubated 1 hour at 37° C. After that, 1 ml of a suspension of $10^8$ pathogenic bacteria (*S. aureus*) in DMEM was added to the cultures and incubated 1 hour more at 37° C. The cells were washed twice with PBS and fixed with ice-cold 70% methanol for 30 minutes. Plates were air dried and Gram stained. The attached bacteria were visualized using an optical Axiovert 200 (Zeiss) microscope at 1000× magnification in oil-immersion. The number of gram-negative bacteria in 10 randomized fields was counted and the results expressed as the mean of % of pathogenic bacteria attached to the cells compared to control cultures without probiotic strains (FIG. 3B).

Example 3d

Protection of Mastitis

To evaluate the efficacy of the probiotic candidates to protect against mastitis, we used a mice model of this pathology. In brief, 10 Wistar pregnant rats per group were daily supplemented by oral gavage with $10^8$ cfu/day of each probiotic strain vehiculated in 200 μl of milk during two weeks after labour. One week after labour, mastitis infection was induced in the animals by injection of $10^6$ cfu of S. aureus in the fourth mammary gland pair. Expressed milk was collected at days 0, 5 and 10 post-infection to measure bacterial load (FIG. 4A); and 5 animals of each group were sacrificed at days 5 and 10 post infection in order to obtain mammary gland biopsies to evaluate the inflammatory process by histological examination.

Figure 4:
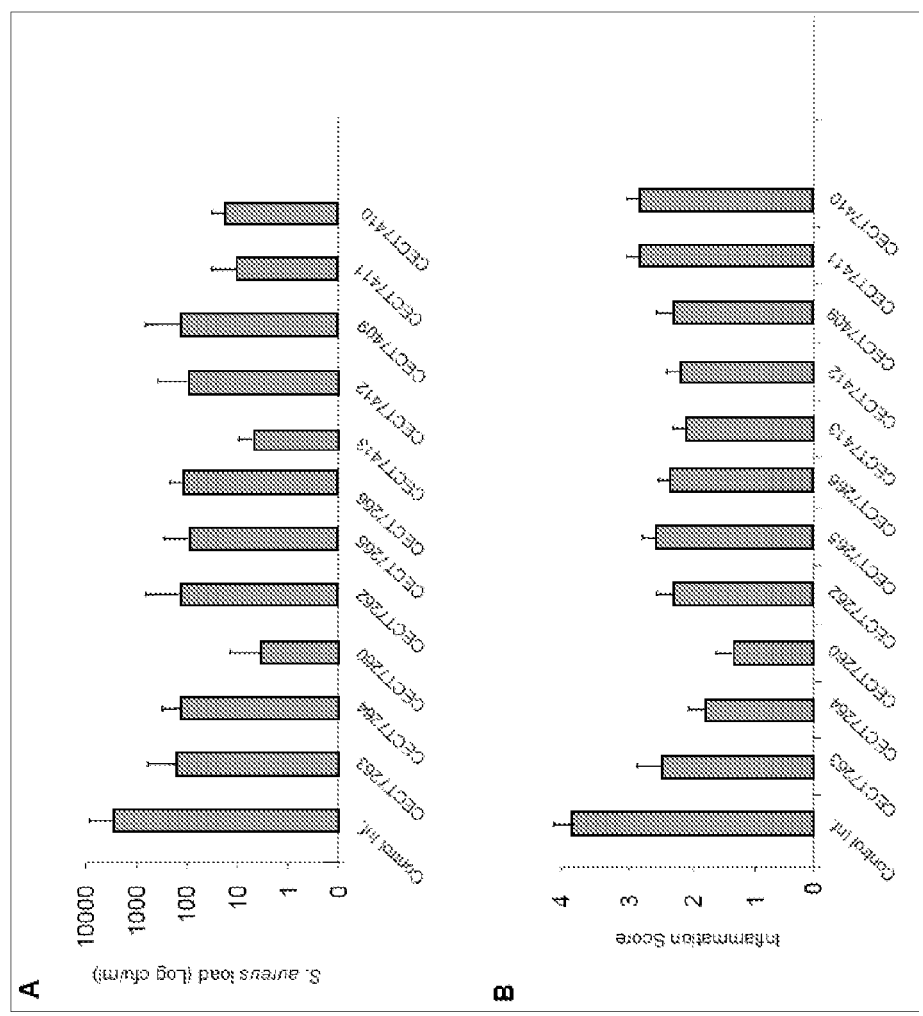
FIG. 4 is a graph bar showing the protection from staphylococcal mastitis. Mastitis was induced in lactating mice 10 days post-parturition by injection of $10^6$ cfu of S. aureus in the fourth mammary pair. Staphylococcal load in the expressed milk (A) and the inflammatory mammary score (B) was evaluated after 5 and 10 days of infection.

Whole glands were fixed in 5% formalin and dehydrated with alcohol, and finally embeded in paraffin. Tissue sections were stained with haematoxylin-eosin an examined in a blinded fashion (FIG. 4B). To qualitatively evaluate alterations of mammary gland histology, an inflammatory index value (IIV) was determined as follow:

Score 0: No infiltration
Score 1: Mild PMN cell interstitial infiltration in isolated areas of tissue sections, undamaged tubular epithelium
Score 2: Interstitial infiltration covering most fields, dispersed areas of tissue damage with loss of tissue structure, and scant images of abscess formation
Score 3: Severe infiltration covering most fields, frequent areas of tissue damage with loss of tissue architecture, and frequent images of abscess formation.

Example 4

Probiotic Potential of the Strains

The selected strains were further analyzed for different characteristics that could enhance their capabilities to act as a probiotic strains. The results obtained are described in the indicated examples.

Example 4a

Adhesion to Caco-2 and HT-29 Cells

For the adhesion assays the cell lines Caco-2 (ATCC HTB-37) and HT-29 (ATCC HTB-38) were utilized as a model of the intestine cells. Both cell lines presented features characteristic for intestinal cells such as polarization, expression of intestinal enzymes, production of particular structural polypeptides and mucins.

The cells were grown in plastic flasks (75 $cm^2$, Nunc) in DMEM as culture medium supplemented with 10% inactivated FCS, non essential amino acids, 100 U/ml penicillin/streptomycin, 1 µg/ml amphotericine. Culturing was performed at 37° C. in an atmosphere comprising 95% air and 5% $CO_2$. Media was changed on a two daily basis and the cells were split every week.

Caco-2 and HT-29 intestinal cell lines were split in 35 mm plastic dishes in 2 ml medium without antibiotics to confluence. 10-14 days post-confluence, 1 ml of media was replaced with 1 ml of a suspension of $10^8$ bacteria in DMEM (PAA). The cultures were incubated 1 hour at 37° C. After that, cells were washed twice with PBS and fixed with ice-cold 70% methanol for 30 minutes. Plates were air dried and Gram stained.

Figure 5:
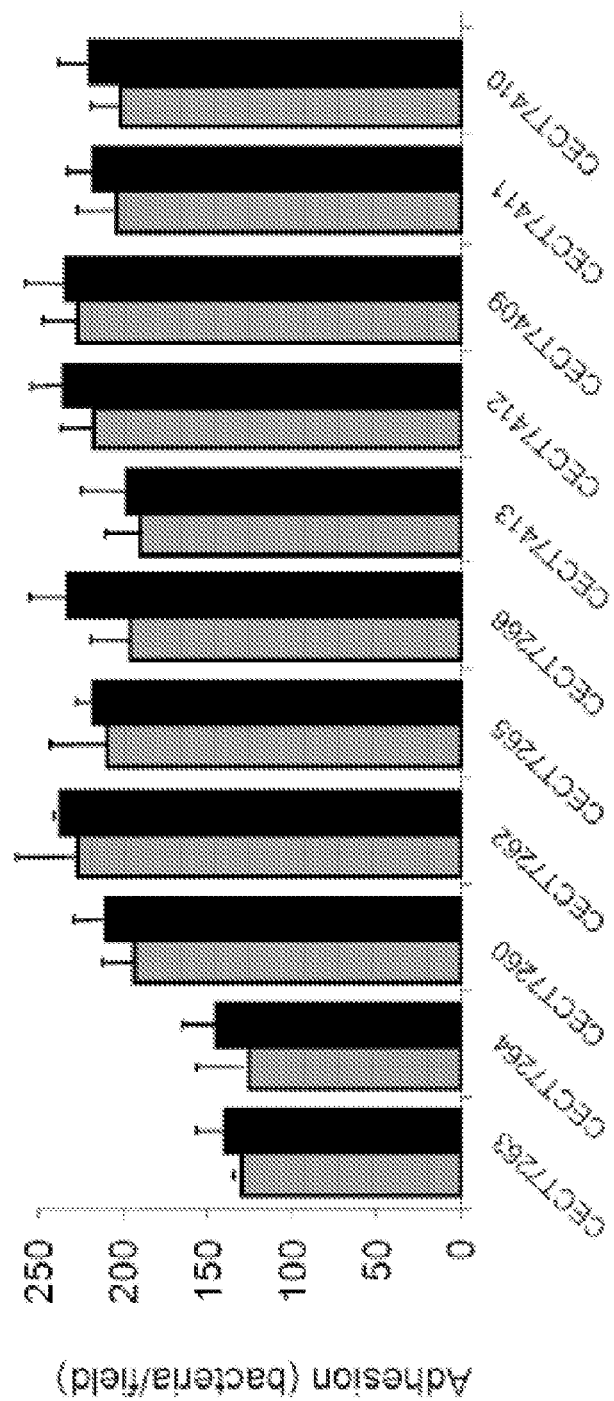
FIG. 5 is a graph bar showing the adhesion of probiotic strains to intestinal cells. The adhesion of the probiotic strains of this invention was assessed using Caco-2 (grey bars) or HT-29 (black bars) intestinal cell lines. Twenty randomized fields were counted and the results expressed as the mean of the number of bacteria attached to the cells per field ±SD.

The attached bacteria were visualized using an optical Axiovert 200 (Zeiss) microscope at 1000× magnification in oil-immersion. Twenty randomized fields were counted and the results expressed as the mean of the number of bacteria attached to the cells per field ±SD (FIG. 5)

Example 4b

Resistance to Acid and Bile Salts

Figure 6:
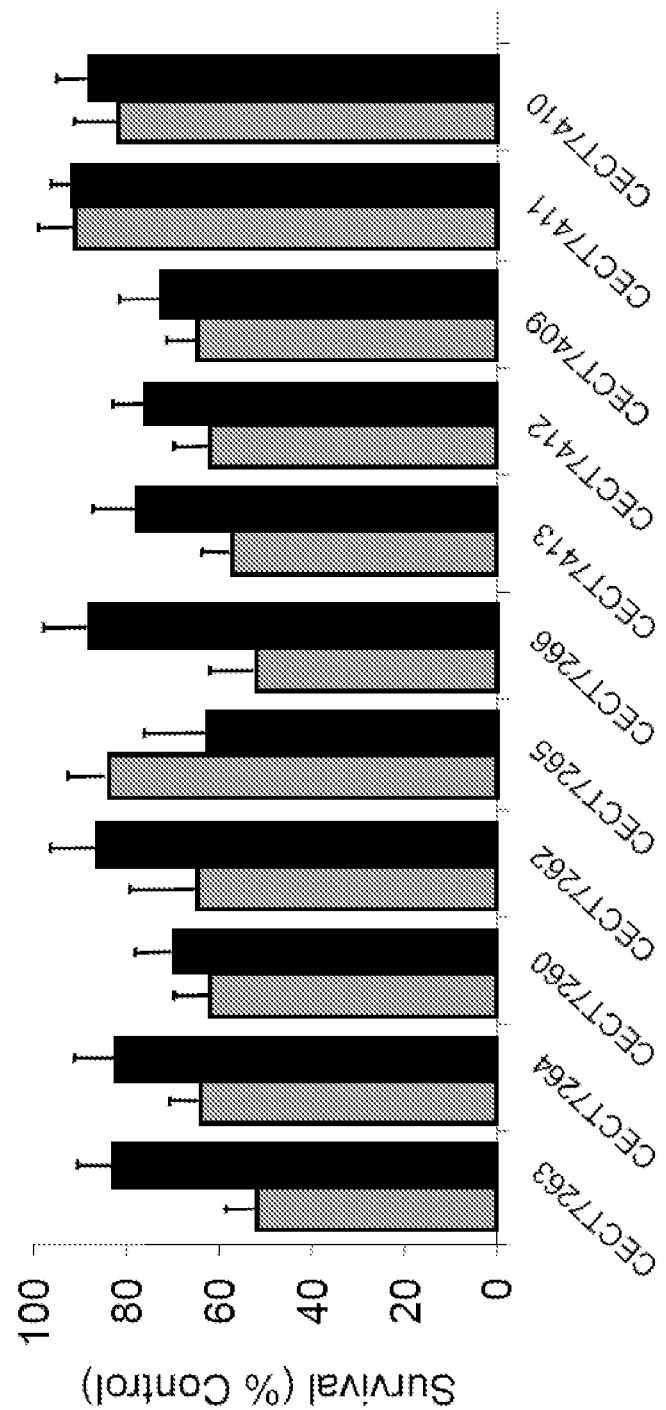
FIG. 6 is a graph bar showing the survival of probiotic strains to digestion-resembling conditions. The resistance of the probiotic strains of this invention to acidic (grey bars) and high bile salt content (black bars) was assessed in vitro by culture of the bacteria in MRS pH 3.0 or 0.15% bile salts for 90 minutes. The results are represented as the mean±SD of three independent experiments.

To analyze the resistance of the probiotic strains of this invention to acidic and high bile salt content, conditions that these bacteria will encounter during the digestive transit, bacteria were cultured in MRS broth medium pH 3.0 or with 2% bile salts (Sigma) for 90 minutes. The survival was calculated by MRS agar plating of serial dilutions and compared to the number of colonies obtained in control conditions (MRS broth pH 5.8). Plates were cultured 24 hours at 36° C. in extreme anaerobic conditions. The experiment was repeated three times (FIG. 6).

Example 4c

Resistance to Antibiotics

The use of modern antibiotics leads to a reduction of the comensal gut microflora which sometimes relates to diarrhoea and other gut disorders. Moreover, this reduction in the amount of gut bacteria could be the consequence of opportunistic pathogenic bacteria and viruses to infect the host. The use of antibiotics to block the infection does not resolve this disorder but complicates it. In other situations like intestinal inflammation where probiotics could exert a beneficial role, this potential effect is sometimes limited for the simultaneous therapy with antibiotics. For all these reasons, the selection of potential probiotic strains which were able to resist common antibiotics should be clearly interesting.

To analyze the resistance of the probiotic strains of this invention we used a agar well diffusion assay. Müeller-Hinton agar plates containing $10^6$ cfu/ml of each probiotic strain were prepared. Then, antibiotic commercial discs were added to the wells and allowed to diffuse into the agar during 10 minutes preincubation period at room temperature, followed by extreme anaerobic incubation of the plates at 36° C. for 16-18 hours.

The antibiotic resistance of the probiotic strains of this invention is summarized in Table II.

TABLE II

Antibiotic resistance of the different probiotic strains of the invention

| | 7263 | 7264 | 7260 | 7262 | 7265 | 7266 | 7413 | 7412 | 7409 | 7411 | 7410 |
|---|---|---|---|---|---|---|---|---|---|---|---|
| Penicillin | S | S | R | S | S | R | R | S | S | S | S |
| Ampicilin | S | S | R | S | S | R | R | S | S | S | S |
| Ciprofloxacin | S | S | S | S | R | S | S | S | S | S | S |
| Erythromycin | S | S | S | S | S | S | S | S | S | S | S |
| Clindamicin | S | S | S | S | S | S | S | S | S | R | R |
| Tetracycline | S | S | S | S | S | S | S | S | S | S | R |
| Vancomycin | S | S | R | R | R | R | R | R | R | S | S |
| Gentamicin | R | R | S | S | R | S | S | S | S | S | S |
| Cloramphenicol | S | S | S | S | S | S | S | S | S | S | S |
| Rifampicine | S | S | S | S | S | S | S | S | S | S | R |

Example 4d

Production of Antimicrobial Metabolites

It has been suggested that the main mechanism used by probiotics is controlling the balance between useful and harmful intestinal bacteria is the gut. When the number of useful bacteria is reduced, opportunistic bacteria could overgrow and disturb the well-being of the host or even induce an infection. Most bacterial organisms have acquired characteristics or mechanisms that reduce the growth capabilities of other microorganisms that cohabitate with them and thus, enabling their selective growth. The reduction of pH through acid production by lactic acid bacteria is one of such mechanisms. Moreover, some lactic acid bacteria also produce bioactive peptides components and other metabolites that selective inhibit the growth of other bacteria, yeast or fungi. This is the case of reuterin (an aldehyde) or bacteriocins (peptides, such as nisin or pediocin PA-1).

The probiotic strains of this invention were assessed for their capability to produce bactericidal metabolites using an agar well diffusion assay. TSA agar plates containing $10^6$ cfu/ml of different pathogenic bacteria strain were prepared and assayed as previously indicated in Example 3b for *S. aureus*. Results obtained were described in Table III.

TABLE III pathogen inhibitory potential of the different probiotic strains of the invention

| | 7413 | 7412 | 7409 | 7411 | 7410 | 7263 | 7264 | 7260 | 7262 | 7265 | 7266 |
|---|---|---|---|---|---|---|---|---|---|---|---|
| *E. faecium* P21 | + | + | + | − | − | +++ | +++ | + | + | +++ | +++ |
| *E. faecalis* TAB28 | +++ | +++ | +++ | − | − | ++ | +++ | +++ | +++ | +++ | +/− |
| *L. monocytogenes* Scott A | ++ | +/− | + | +/− | +/− | +++ | ++ | ++ | +/− | + | +++ |
| *L. innocua* RdC | + | +/− | + | +/− | +/− | ++ | ++ | +/− | + | +/− | +/− |
| *E. coli* CECT 4076 | +++ | +++ | +++ | + | + | +++ | + | +++ | +++ | +++ | +++ |
| *E. coli* RJM1 | +++ | +++ | +++ | + | + | + | +++ | ++ | +++ | +++ | +/− |
| *S. enteritidis* 4396 | +++ | +++ | +++ | ++ | ++ | +/− | ++ | ++ | +++ | +++ | ++ |
| *K. pneumoniae* CECT142 | ++ | +++ | +++ | +++ | +++ | +++ | + | ++ | + | +++ | ++ |
| *K. oxytoca* CECT860T | +/− | + | +++ | ++ | ++ | +++ | +++ | +/− | +/− | +/− | ++ |
| *P. vulgaris* CECT484 | ++ | ++ | ++ | + | + | +/− | + | +++ | +++ | +++ | +/− |
| *S. aureus* CECT5191 | +++ | +++ | +++ | ++ | ++ | +++ | +++ | +++ | ++ | +++ | +++ |
| *S. epidermidis* CECT231 | ++ | ++ | +++ | ++ | ++ | ++ | +++ | +++ | ++ | ++ | ++ |

Example 5

Effect of the Probiotic Strains of this Invention on Translocation of *Salmonella typhimurium* in Mice Following Immunization with Inactivated *Salmonella* Vaccine Translocation of gram-negative bacteria across the gut epithelium can occur especially in subjects following gastrointestinal infection, disease or surgery. Left untreated it can lead to endotoxemia. In this example, the effect of feeding the probiotic strains of this invention on the translocation of the gut pathogen *Salmonella typhimurium* was examined.

Male Balb/c mice (6-8 weeks old) were daily fasted with $1 \times 10^8$ cfu in 0.2 ml of milk or milk alone for two weeks. After that, mice were either orally immunized or not with an inactivated *Salmonella* vaccine ($10^8$ cfu inactivated with paraphormaldehyde in 0.2 ml milk). After immunization, mice were fasted two weeks more with the probiotic preparations in alternate days for two weeks more. Two weeks after oral immunization, all mice were orally challenged with live *S. typhimurium* ($10^{10}$ cfu in 0.2 ml milk).

Then, after 24-48 hours, the level of colonization of *S. typhimurium* in the spleen was determined in half of the animals. The rest of the animals were followed during two additional weeks in order to evaluate the survival of the animals after *Salmonella* infection.

The results obtained demonstrate that most of the probiotics tested potentiates the beneficial effect of the vaccination of mice with the inactivated *Salmonella* vaccine as shown in FIG. 7.

Example 6

Effect of *L. plantarum* CECT7262 or *L. reuteri* CECT7260 on the Prevention of Neonatal Diarrhoea in Neonatal Piglets The weaning of piglets at 3-4 weeks of age correlates with a high mortality rate in those animals mainly due to an increase in the incidence of diarrhoeal infections. Probably, this high mortality relates to a down-regulation of their defences due to the stressing modification of their nutritional and management status and to important changes in the composition of their gut microbiota.

For this reason, farmers have tried to solve this problem with the use of several approaches such as the use of antibiotics, immune-stimulant or mucosal protector components, such as colistine or ZnO. However, the EU ban of the use of antibiotics for animal production in 2006 has aggravated the situation. For this reason, the use of probiotics able to modulate the gut microbiota and the immune response appears as a potential alternative.

We compared the protective effect of the administration of $3 \times 10^9$ cfu/day of *L. reuteri* CECT7260 and *L. plantarum* CECT7262 versus the administration of an animal feed formulation containing 3000 ppm of ZnO and 40 ppm colistine in two groups of 48 and 45, respectively, weaned pigs for a period of 34 days.

In both groups, none of the animals suffered from diarrhoea nor died during the study, and the evolution of the body weight was also similar between both treatments, suggesting that an animal feed formulation supplemented with these probiotics is, at least, as good as those containing conventional antibiotics and immune modulators.

Example 7

Effect of Probiotic Bacteria on Inflammatory Cytokines and IgG Production

Besides the reduction of the risk of infection, many clinical effects associated to probiotic treatments are due to immuno-modulatory capabilities of selected probiotic strains. The regulation of the immune response is usually mediated through a change in the balance between pro-inflammatory cytokines (Th1) such as TNF-α, humoral cytokines (Th2) such as IL-4 or IL-13, and regulatory cytokines (Th3) such as IL-10 and TGF-β. Moreover, the bias in the immune response will also modulate the secretion of immunoglobulins during the subsequent humoral response. For this reason, we have also tested the effect of some of the probiotic strains of this invention in regulating the expression of some of these clue cytokines and IgG.

We have used bone marrow-derived macrophages stimulated with 100 ng/ml of LPS (Sigma) as a cellular model. $10^5$ macrophages/well were cultured in 24-well plastic plates (Nunc) with 1 ml of DMEM. Once attached, macrophages were stimulated or not with 100 ng/ml LPS and with $10^7$ cfu/ml of the indicated probiotic strains for 12 hours at 37° C. in a 5% $CO_2$ atmosphere. Supernatants were collected and the production of cytokines was analyzed using a mouse TNF-α or mouse IL-10 ELISA (Biosource). The results obtained are summarized in FIGS. 8A and B.

Figure 8:
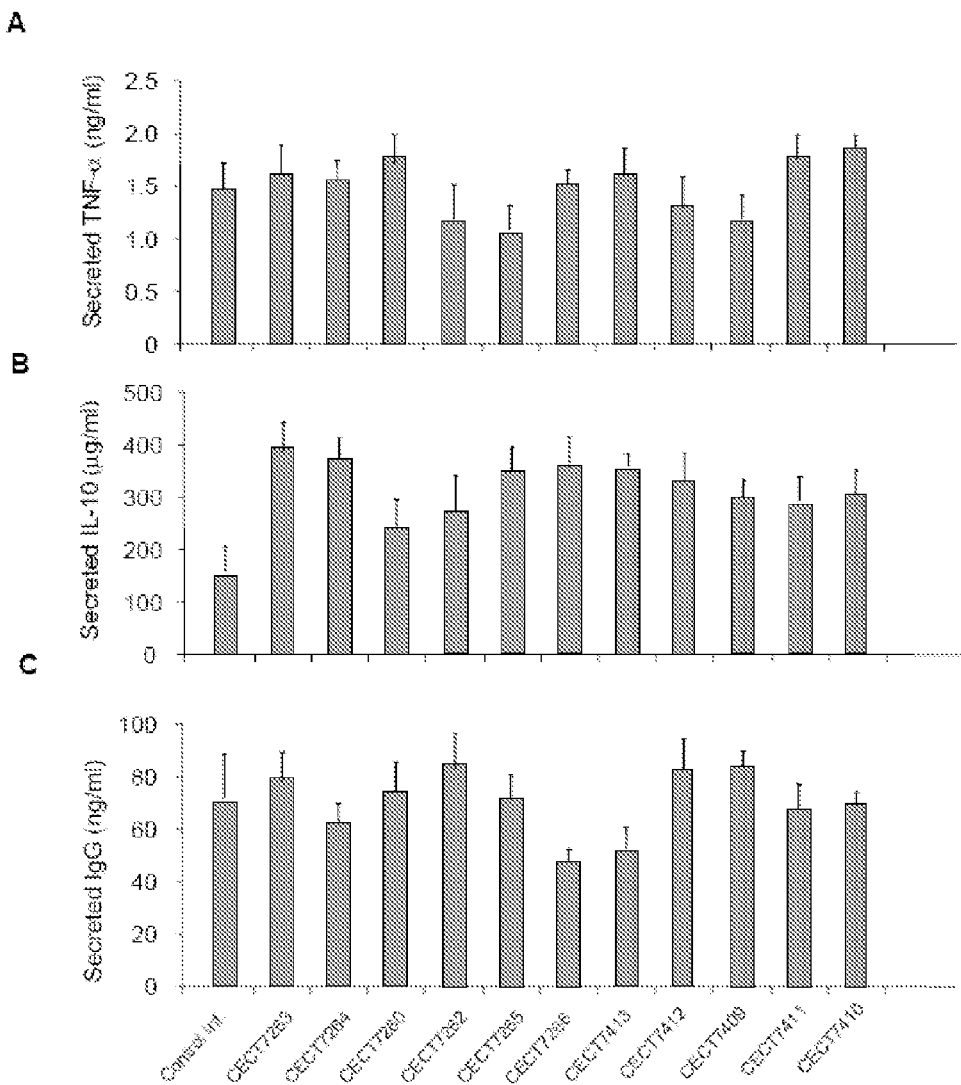
FIG. 8 is a graph bar showing the effect of probiotic strains on cytokine and immunoglobulin G expression. The TNF-α (A) and IL-10 (B) cytokine production was analyzed in bone marrow-derived macrophages stimulated with LPS and the indicated probiotic strain for 12 hours while IgG expression (C) was analyzed in lymphocytes obtained from the spleen of Balb/c mice (6-8 weeks old) stimulated with LPS and the indicated probiotic strain for 6 days. Both cytokine and IgG production were detected by ELISA.

The analysis of the effect of the probiotic strains of this invention on immunoglobulin production was performed using lymphocyte cultures obtained from the spleen of male Balb/c mice (6-8 weeks old). $2\times10^6$ lymphocytes were cultured in 1 ml DMEM in 24 well plastic plates and stimulated with inactivated probiotic cultures ($10^8$ cfu/ml) in presence or absence of 25 µg/ml LPS for 6 days. The production of IgG by lymphocytes was assessed using a mouse IgG ELISA from Bethyl (FIG. 8C).

The invention claimed is:

1. A probiotic strain or a mixture of strains consisting of lactic acid bacteria or bifidobacteria strains present in the fresh milk from a mammalian species selected in lactic acid culture media, wherein said probiotic strain or mixture of strains (i) are capable of being transferred to the mammary gland after oral intake and/or colonise the mammary gland after its topical application, (ii) are able to reduce the rates of survival and/or the rates of adhesion to epithelial cells of *Staphylococcus aureus*, and (iii) capable of protecting animals from mastitis, characterised in that the strain is selected from the group consisting of *Bifidobacterium breve* deposited in the CECT under Accession No. 7263, *Bifidobacterium breve* deposited in the CECT under Accession No. 7264, *Lactobacillus reuteri* deposited in the CECT under Accession No. 7260, *Lactobacillus plantarum* deposited in the CECT under Accession No. 7262, *Lactobacillus fennenturn* in the CECT under Accession No. 7265 and *Lactobacillus reuteri* deposited in the CECT under Accession No. 7266, *Enterococcus hirae* deposited in the CECT under Accession No. 7410, *Lactobacillus plantarum* deposited in the CECT under Accession No. 7412, *Enterococcus faecalis* deposited in the CECT under Accession No. 7411, *Lactobacillus salivarius* deposited in the CECT under Accession No. 7409, *Lactobacillus reuteri* deposited in the CECT under Accession No. 7413.

2. A pharmaceutical composition comprising at least a probiotic strain according to claim 1.

3. The composition as defined in claim 2 which is in a frozen, lyophilized or dried form.

4. The composition as defined in claim 2 wherein the probiotic strain or the mixture thereof is in a partially or totally inactivated form.

5. A method of treating mastitis, said method comprising administering an effective amount of the probiotic strain of claim 1 to a subject or animal in need thereof.

6. The method according to claim 5, wherein the strain is administered orally, topically, nasally, enterally, ocularly, urogenitally, rectally, or vaginally.

7. A method of treating neonatal diarrhea, said method comprising administering an effective amount of the probiotic strain of claim 1 to a subject or animal in need thereof.

8. The method according to claim 7, wherein the strain is administered to a lactating woman or animal for the therapeutic or prophylactic treatment of the foetus and/or their breastfed babies or pups.

9. The method according to claim 8, wherein the strain is administered to the lactating woman or animal orally, topically, nasally, enterally, ocularly, urogenitally, rectally, or vaginally.

10. The method according to claim 7, wherein the strain is administered orally, topically, nasally, enterally, ocularly, urogenitally, rectally, or vaginally.

* * * * *